US008795958B2

(12) United States Patent
Collins et al.

(10) Patent No.: US 8,795,958 B2
(45) Date of Patent: Aug. 5, 2014

(54) IN VIVO GENE SENSORS

(71) Applicants: Trustees of Boston University, Boston, MA (US); Massachusetts Institute of Technology, Cambridge, MA (US)

(72) Inventors: James J. Collins, Newton, MA (US); Timothy Kuan-Ta Lu, Charlestown, MA (US)

(73) Assignees: Trustees of Boston University, Boston, MA (US); Massachusetts Institute of Technology, Boston, MA (US)

( * ) Notice: Subject to any disclaimer, the term of this patent is extended or adjusted under 35 U.S.C. 154(b) by 0 days.

(21) Appl. No.: 13/661,169

(22) Filed: Oct. 26, 2012

(65) Prior Publication Data

US 2013/0053432 A1    Feb. 28, 2013

Related U.S. Application Data

(63) Continuation of application No. 12/867,537, filed as application No. PCT/US2009/034296 on Feb. 17, 2009, now Pat. No. 8,329,889.

(60) Provisional application No. 61/029,158, filed on Feb. 15, 2008.

(51) Int. Cl.
*C12Q 1/68* (2006.01)
(52) U.S. Cl.
USPC .............................. 435/6; 435/325; 435/375
(58) Field of Classification Search
None
See application file for complete search history.

(56) References Cited

U.S. PATENT DOCUMENTS

| | | |
|---|---|---|
| 2003/0064931 A1 | 4/2003 | Gallivan |
| 2003/0166879 A1 | 9/2003 | Gardner et al. |
| 2005/0053951 A1 | 3/2005 | Breaker et al. |
| 2006/0088864 A1 | 4/2006 | Smolke et al. |
| 2006/0140911 A1 | 6/2006 | Sharp et al. |
| 2007/0136827 A1 | 6/2007 | Collins et al. |

FOREIGN PATENT DOCUMENTS

| | | |
|---|---|---|
| WO | 01/00815 | 1/2001 |
| WO | 03/078575 | 9/2003 |
| WO | 2006/088165 A1 | 8/2006 |

OTHER PUBLICATIONS

Bamor et al, "Intracellular expression of antisense RNA transcripts complementary to the human immunodeficiency virus type-1 vif gene inhibits viral replication in infected T-lymphoblastoid cells", vol. 320, No. 2, pp. 544-550, 2004.
Brown et al, "Endogenous microRNA regulation suppresses transgene expression in hematopoietic lineages and enables stable gene transfer", Nature Medicine, vol. 12, No. 5, pp. 585-591, 2006.
Care et al, "MicroRNA-133 controls cardiac hypertrophy", Nature Medicine, vol. 13, No. 5, pp. 613-618, 2007.
Deans et al, "A Tunable Genetic Switch Based on RNAi and Repressor Proteins for Regulating Gene Expression in Mammalian Cells", Cell, vol. 130, No. 2, pp. 363-372, 2007.
Ebert et al, "MicroRNA sponges: competitive inhibitors of small RNAs in mammalian cells", Nature Methods, vol. 4, No. 9, pp. 721-726, 2007.
Gardner et al, "Construciton of a genetic toggle switch in *Escherichia coli*", Nature, vol. 403, No. 6767, pp. 339-342, 2000.
Isaacs et al, "Engineered riboregulators enable post-transcriptional control of gene expression", Nature Biotechnology, vol. 22, No. 7, pp. 841-847, 2004.
Nakashima et al, "Paired termini stabilize antisense RNAs and enhance conditional gene silencing in *Escherichia coli*", Nucleic Acids Research, vol. 34, No. 20, pp. 1-10, 2006.
Sando et al, "Doubly Catalytic Sensing of HIV-1-Related CCR5 Sequence in Prokaryotic Cell-Free Translation System using Riboregulator-Controlled Luciferase Activity", J. of Am. Chem. Soc., vol. 127, No. 16, pp. 5300-5301, 2005.
Vohlander Rasmussen et al, "Hittling bacteria at the heart of the central dogma: sequence-specific inhibition", Microbial Cell Factories, vol. 6, No. 1, pp. 1-26, 2007.
Xiao et al, "Novel Approaches for Gene-Specific Interference Via Manipulating Actions of MicroRNAs: Examination on the Pacemaker Channel Genes HCN2 and HCN4", J. of Cell. Phys., vol. 212, No. 2, pp. 285-292, 2007.
Slootweg et al. (NAR 2006: e1-e11).
Kaplen et al. (J. Bact. 2004, vol. 186: pp. 8213-8220).
Nakashima et al. Nucleic Acids Research 2006.

*Primary Examiner* — Kimberly Chong
(74) *Attorney, Agent, or Firm* — Mark J. FitzGerald; Nixon Peabody LLP

(57) ABSTRACT

Described are methods and compositions for the detection of target genes. The inventors have developed a synthetic nucleic acid sensor-effector gene circuit. In cells without a target gene, the circuit suppresses e.g., effector production, but in the presence of the target gene the suppression is subject to competition, such that the synthetic sensor is derepressed and permits expression of the effector gene. The methods and compositions described further permit the selective expression of an effector gene in those cells expressing the target gene. In this manner, cells expressing a target gene can be selectively targeted for treatment or elimination. In certain aspects, the methods and compositions described permit the selective expression of an agent such as a therapeutic gene product, in a specifically targeted population of cells in an organism.

16 Claims, 9 Drawing Sheets

Figure 6.

**Chloramphenicol acetyltransferase (*cat*)**

atggagaaaaaaatcactggatataccaccgttgatatatcccaatggcatcgtaaagaaca
ttttgaggcatttcagtcagttgctcaatgtacctataaccagaccgttcagctggatatta
cggccttttttaaagaccgtaaagaaaaataagcacaagttttatccggcctttattcacatt
cttgcccgcctgatgaatgctcatccggaattccgtatggcaatgaaagacggtgagctggt
gatatgggatagtgttcaccttgttacaccgttttccatgagcaaactgaaacgttttcat
cgctctggagtgaataccacgacgatttccggcagttttctacacatatattcgcaagatgtg
gcgtgttacggtgaaaacctggcctatttccctaaagggtttattgagaatatgttttttcgt
ctcagccaatccctgggtgagtttcaccagttttgatttaaacgtggccaatatggacaact
tcttcgccccgttttcaccatgggcaaatattatacgcaaggcgacaaggtgctgatgccg
ctggcgattcaggttcatcatgccgtctgtgatggcttccatgtcggcagaatgcttaatga
attacaacagtactgcgatgagtggcagggcggggcgtaa

**Tetracycline resistance (*tetR*)**

```
  1 atgtctagat tagataaaag taaagtgatt aacagcgcat tagagctgct taatgaggtc
 61 ggaatcgaag gtttaacaac ccgtaaactc gcccagaagc taggtgtaga gcagcctaca
121 ttgtattggc atgtaaaaaa taagcgggct ttgctcgacg ccttagccat tgagatgtta
181 gataggcacc atactcactt ttgcccttta gaaggggaaa gctggcaaga tttttttacgt
241 aataacgcta aagttttag atgtgcttta ctaagtcatc gcgatggagc aaaagtacat
301 ttaggtacac ggcctacaga aaacagtat gaaactctcg aaaatcaatt agccttttta
361 tgccaacaag gtttttcact agagaatgca ttatatgcac tcagcgctgt ggggcatttt
421 actttaggtt gcgtattgga agatcaagag catcaagtcg ctaaagaaga aagggaaaca
481 cctactactg atagtatgcc gccattatta cgacaagcta tcgaattatt tgatcaccaa
541 ggtgcagagc cagccttctt attcggcctt gaattgatca tatgcggatt agaaaaacaa
601 cttaaatgtg aaagtgggtc ttaa
```

**Kanamycin resistance (*kan*)**

ATGATTGAACAAGATGGATTGCACGCAGGTTCTCCGGCCGCTTGGGTGGAGAGGCTATTCGGCTATGACTGGGCA
CAACAGACAATCGGCTGCTCTGATGCCGCCGTGTTCCGGCTGTCAGCGCAGGGGCGCCCGGTTCTTTTTGTCAAG
ACCGACCTGTCCGGTGCCCTGAATGAACTGCAGGACGAGGCAGCGCGGCTATCGTGGCTGGCCACGACGGGCGTT
CCTTGCGCAGCTGTGCTCGACGTTGTCACTGAAGCGGGAAGGGACTGGCTGCTATTGGGCGAAGTGCCGGGGCAG
GATCTCCTGTCATCTCACCTTGCTCCTGCCGAGAAAGTATCCATCATGGCTGATGCAATGCGGCGGCTGCATACG
CTTGATCCGGCTACCTGCCCATTCGACCACCAAGCGAAACATCGCATCGAGCGAGCACGTACTCGGATGGAAGCC
GGTCTTGTCGATCAGGATGATCTGGACGAAGAGCATCAGGGGCTCGCGCCAGCCGAACTGTTCGCCAGGCTCAAG
GCGCGCATGCCCGACGGCGAGGATCTCGTCGTGACCCATGGCGATGCCTGCTTGCCGAATATCATGGTGGAAAAT
GGCCGCTTTTCTGGATTCATCGACTGTGGCCGGCTGGGTGTGGCGGACCGCTATCAGGACATAGCGTTGGCTACC
CGTGATATTGCTGAAGAGCTTGGCGGCGAATGGGCTGACCGCTTCCTCGTGCTTTACGGTATCGCCGCTCCCGAT
TCGCAGCGCATCGCCTTCTATCGCCTTCTTGACGAGTTCTTCTGA

`Ampicillin resistance (bla)`

ATGAGTATTCAACATTTCCGTGTCGCCCTTATTCCCTTTTTTGCGGCATTTTGCCTTCCTGTTTTTGCTCACCCA
GAAACGCTGGTGAAAGTAAAAGATGCTGAAGATCAGTTGGGTGCACGAGTGGGTTACATCGAACTGGATCTCAAC
AGCGGTAAGATCCTTGAGAGTTTTCGCCCCGAAGAACGTTTTCCAATGATGAGCACTTTTAAAGTTCTGCTATGT
GGCGCGGTATTATCCCGTATTGACGCCGGGCAAGAGCAACTCGGTCGCCGCATACACTATTCTCAGAATGACTTG
GTTGAGTACTCACCAGTCACAGAAAAGCATCTTACGGATGGCATGACAGTAAGAGAATTATGCAGTGCTGCCATA
ACCATGAGTGATAACACTGCGGCCAACTTACTTCTGACAACGATCGGAGGACCGAAGGAGCTAACCGCTTTTTTG
CACAACATGGGGGATCATGTAACTCGCCTTGATCGTTGGGAACCGGAGCTGAATGAAGCCATACCAAACGACGAG
CGTGACACCACGATGCCTGTAGCAATGGCAACAACGTTGCGCAAACTATTAACTGGCGAACTACTTACTCTAGCT
TCCCGGCAACAATTAATAGACTGGATGGAGGCGGATAAAGTTGCAGGACCACTTCTGCGCTCGGCCCTTCCGGCT

Figure 6. (cont)

```
GGCTGGTTTATTGCTGATAAATCTGGAGCCGGTGAGCGTGGGTCTCGCGGTATCATTGCAGCACTGGGGCCAGAT
GGTAAGCCCTCCCGTATCGTAGTTATCTACACGACGGGGAGTCAGGCAACTATGGATGAACGAAATAGACAGATC
GCTGAGATAGGTGCCTCACTGATTAAGCATTGGTAA
```

Vancomycin resistance (vanA, vanH, vanX required and shown in order)

vanA

```
   1 atgaatagaa taaaagttgc aatactgttt ggggttgct cagaggagca tgacgtatcg
  61 gtaaaatctg caatagagat agccgctaac attaataaag aaaaatacga gccgttatac
 121 attggaatta cgaaatctgg tgtatggaaa atgtgcgaaa aaccttgcgc ggaatgggaa
 181 aacgacaatt gctattcagc tgtactctcg ccggataaaa aaatgcacgg attacttgtt
 241 aaaaagaacc atgaatatga aatcaaccat gttgatgtag cattttcagc tttgcatggc
 301 aagtcaggtg aagatggatc catacaaggt ctgtttgaat tgtccggtat cccttttgta
 361 ggctgcgata ttcaaagctc agcaatttgt atggacaaat cgttgacata catcgttgcg
 421 aaaaatgctg ggatagctac tccggccttt tgggttatta ataaagatga taggccggtg
 481 gcagctacgt ttacctatcc tgttttttgtt aagccggcgc gttcaggctc atccttcggt
 541 gtgaaaaaag tcaatagcgc ggacgaattg gactacgcaa ttgaatcggc aagacaatat
 601 gacagcaaaa tcttaattga gcaggctgtt tcgggctgtg aggtcggttg tgcggtattg
 661 ggaaacagtg ccgcgttagt tgttggcgag gtggaccaaa tcaggctgca gtacggaatc
 721 tttcgtattc atcaggaagt cgagccggaa aaaggctctg aaaacgcagt tataaccgtt
 781 cccgcagacc tttcagcaga ggagcgagga cggatacagg aaacggcaaa aaaaatatat
 841 aaagcgctcg gctgtagagg tctagcccgt gtggatatgt ttttacaaga taacggccgc
 901 attgtactga acgaagtcaa tactctgccc ggtttcacgt catacagtcg ttatcccgt
 961 atgatggccg ctgcaggtat tgcacttccc gaactgattg accgcttgat cgtattagcg
1021 ttaaaggggt ga
//
``` vanH

```
   1 atgaataaca tcggcattac tgtttatgga tgtgagcagg atgaggcaga tgcattccat
  61 gctctttcgc ctcgctttgg cgttatggca acgataatta acgccaacgt gtcggaatcc
 121 aacgccaaat ccgcgcctttt caatcaatgt atcagtgtgg gacataaatc agagatttcc
 181 gcctctattc ttcttgcgct gaagagagcc ggtgtgaaat atatttctac ccgaagcatc
 241 ggctgcaatc atatagatac aactgctgct aagagaatgg gcatcactgt cgacaatgtg
 301 gcgtactcgc cggatagcgt tgccgattat actatgatgc taattcttat ggcagtacgc
 361 aacgtaaaat cgattgtgcg ctctgtggaa aaacatgatt tcaggttgga cagcgaccgt
 421 ggcaaggtac tcagcgacat gacagttggt gtggtgggaa cgggccagat aggcaaagcg
 481 gttattgagc ggctgcgagg atttggatgt aaagtgttgg cttatagtcg cagccgaagt
 541 atagaggtaa actatgtacc gtttgatgag ttgctgcaaa atagcgatat cgttacgctt
 601 catgtgccgc tcaatacgga tacgcactat attatcagcc acgaacaaat acagagaatg
 661 aagcaaggag catttcttat caatactggg cgcggtccac ttgtagatac ctatgagttg
 721 gttaaagcat tagaaaacgg gaaactgggc ggtgccgcat ggatgtatt ggaaggagag
 781 gaagagtttt tctactctga ttgcacccaa aaaccaattg ataatcaatt tttacttaaa
 841 cttcaaagaa tgcctaacgt gataatcaca ccgcatacgg cctattatac cgagcaagcg
 901 ttgcgtgata ccgttgaaaa aaccattaaa actgtttgg attttgaaag gagacaggag
 961 catgaatag
//
``` vanX

```
   1 atggaaatag gatttacttt tttagatgaa atagtacacg gtgttcgttg ggacgctaaa
  61 tatgccactt gggataattt caccggaaaa ccggttgacg gttatgaagt aaatcgcatt
 121 gtagggacat acgagttggc tgaatcgctt ttgaaggcaa aagaactggc tgctacccaa
 181 gggtacggat tgcttctatg ggacggttac cgtcctaagc gtgctgtaaa ctgtttttatg
 241 caatgggctg cacagccgga aaataacctg acaaaggaaa gttattatcc caatattgac
 301 cgaactgaga tgatttcaaa aggatacgtg gcttcaaaat caagccatag ccgcggcagt
 361 gccattgatc ttacgcttta tcgattagac acgggtgagc ttgtaccaat ggggagccga
 421 tttgatttta tggatgaacg ctctcatcat gcggcaaatg gaatatcatg caatgaagcg
 481 caaaatcgca gacgtttgcg ctccatcatg gaaacagtg ggtttgaagc atatagcctc
 541 gaatggtggc actatgtatt aagagacgaa ccatacccca atagctattt tgatttcccc
 601 gttaaataa
//
```

Figure 6. (cont)

**Methicillin-resistance (*mecA*)**http://www.ncbi.nlm.nih.gov/About/disclaimer.html

```
atgaaaaagataaaaattgttccacttatttaatagttgtagttgtcgggtttggtatatatttttatgcttca
aaagataaagaaattaataatactattgatgcaattgaagataaaaatttcaaacaagtttataaagatagcagt
tatatttctaaaagcgataatggtgaagtagaaatgactgaacgtccgataaaaatatataatagtttaggcgtt
aaagatataaacattcaggatcgtaaaataaaaaaagtatctaaaaataaaaaacgagtagatgctcaatataaa
attaaaacaaactacggtaacattgatcgcaacgttcaatttaattttgttaaagaagatggtatgtggaagtta
gattgggatcatagcgtcattattccaggaatgcagaaagaccaaagcatacatattgaaaatttaaaatcagaa
cgtggtaaaatttagaccgaaacaatgtggaattggccaatacaggaacagcatatgagataggcatcgttcca
aagaatgtatctaaaaaagattataaagcaatcgctaaagaactaagtatttctgaagactatatcaaacaacaa
atggatcaaaattgggtacaagatgatacctcgttccacttaaaaccgttaaaaaaatggatgaatatttaagt
gatttcgcaaaaaaatttcatcttacaactaatgaaacagaaagtcgtaactatcctctaggaaaagcgacttca
catctattaggttatgttggtcccattaactctgaagaattaaaacaaaaagaatataaaggctataaagatgat
gcagttattggtaaaaagggactcgaaaaactttacgataaaaagctccaacatgaagatggctatcgtgtcaca
atcgttgacgataatagcaatacaatcgcacatacattaatagagaaaaagaaaaaagatggcaaagatattcaa
ctaactattgatgctaaagttcaaaagagtatttataacaacatgaaaaatgattatggctcaggtactgctatc
caccctcaaacaggtgaattattagcacttgtaagcacaccttcatatgacgtctatccattatgtatggcatg
agtaacgaagaatataataaattaaccgaagataaaaaagaacctctgctcaacaagttccagattacaacttca
ccaggttcaactcaaaaaatattaacagcaatgattgggttaaataacaaaacattagacgataaaacaagttat
aaaatcgatggtaaaggttggcaaaaagataaatcttggggtggttacaacgttacaagatatgaagtggtaaat
ggtaatatcgacttaaaacaagcaatagaatcatcagataacattttctttgctagagtagcactcgaattaggc
agtaagaaatttgaaaaaggcatgaaaaaactaggtgttggtgaagatataccaagtgattatccatttataat
gctcaaattcaaacaaaaatttagataatgaaatattattagctgattcaggttacggacaaggtgaaatactg
attaaccagtacagatcctttcaatctatagcgcattagaaaataatggcaatattaacgcacctcacttatta
aaagacacgaaaacaaagtttggaagaaaaatattatttccaaagaaaatatcaatctattaactgatggtatg
caacaagtcgtaaataaaacacataagaagatatttatagatcttatgcaaacttaattggcaaatccggtact
gcagaactcaaaatgaaacaaggagaaactggcagacaaattgggtggtttatatcatatgataaagataatcca
aacatgatgatggctattaatgttaaagatgtacaagataaaggaatggctagctacaatgccaaaatctcaggt
aaagtgtatgatgagctatatgagaacggtaataaaaaatacgatatagatgaataa
```

IN VIVO GENE SENSORS

CROSS-REFERENCE TO RELATED APPLICATIONS

This application is a Continuation Application of U.S. application Ser. No. 12/867,537 which is a 35 U.S.C. §371 National Phase Entry application of International Application No. PCT/US2009/034296, filed on Feb. 17, 2009, which designates the United States, and which claims the benefit of priority under 35 U.S.C. §119(e) of U.S. Provisional Application No. 61/029,158 filed on Feb. 15, 2008, the contents of which are incorporated herein by reference in their entirety.

GOVERNMENT SUPPORT

This invention was made with Government Support under Contract No. EF-0425719 awarded by the National Science Foundation. The Government has certain rights in the invention.

SEQUENCE LISTING

The instant application contains a Sequence Listing which has been submitted in ASCII format via EFS-Web and is hereby incorporated by reference in its entirety. Said ASCII copy, created on Apr. 8, 2009, is named 701586-061581PCT_ST25.txt and is 20,480 bytes in size.

FIELD OF THE INVENTION

The present invention relates to the detection of cells expressing a target gene.

BACKGROUND OF THE INVENTION

Bacteria rapidly develop resistance to antibiotic drugs within years of their introduction to the clinic[1]. Antibiotic resistance can be acquired by horizontal gene transfer or can result from persistence, in which a small fraction of cells in a population exhibits a non-inherited tolerance to antimicrobials[2]. Since antimicrobial drug discovery is lagging behind the evolution of antibiotic resistance, there is a pressing need for new antibacterial therapies[3].

Bacterial infections are responsible for significant morbidity and mortality in clinical settings[3]. Though the advent of antibiotics has reduced the impact of bacterial diseases on human health, the constant evolution of antibiotic resistance poses a serious challenge to the usefulness of currently available antibiotic drugs[3-7]. Infections that would have been easily cured by antibiotics in the past are now able to survive to a greater extent, resulting in sicker patients and longer hospitalizations[5, 8, 9]. The economic impact of antibiotic-resistant infections is estimated to be between US $5 billion and US $24 billion per year in the United States alone[10]. Resistance to antibiotic drugs develops and spreads rapidly, often within a few years of first clinical use[1]. However, the introduction of new agents to the market by pharmaceutical companies has not kept pace with the evolution of antibiotic resistance[1,3].

Acquired antibiotic resistance results from mutations in antibacterial targets or from genes encoding conjugative proteins that pump antibiotics out of cells or inactivate antibiotics[11]. Horizontal gene transfer, which can occur via transformation, conjugative plasmids, or conjugative transposons, is a major mechanism for the spread of antibiotic resistance genes[12, 13]. For example, Staphylococcus aureus became quickly resistant to sulpha drugs in the 1940s, penicillin in the 1950s, and methicillin in the 1980s[12]. In 2002, staphylococci developed resistance to vancomycin (the only uniformly effective antibiotic against staphylococci) by receiving vancomycin-resistance genes via conjugation from co-infecting Enterococcus faecalis, which itself became completely resistant to vancomycin in nosocomial settings by 1988[12, 14]. Some agents (e.g., ciprofloxacin) promote the horizontal dissemination of antibiotic resistance genes by mobilizing genetic elements[15, 16]. Streptococcus pneumoniae and Neisseria gonorrhoeae have also obtained resistance to antibiotics (Morens, et al., (2004) Nature 430: 242-249). Sub-inhibitory concentrations or incomplete treatment courses can present evolutionary pressures for the development of antibiotic resistance[17]. Use of antibiotics outside of clinical settings, for example in livestock for the agricultural industry, has contributed to the emergence of resistant organisms such as methicillin-resistant staphylococci and is unlikely to abate due to economic reasons and modern farming practices[12, 18]. Resistance genes that develop in non-clinical settings may be subsequently transmitted to bacterial populations which infect humans, worsening the antibiotic resistance problem[12].

In addition to acquiring antibiotic-resistance genes, a small subpopulation of cells known as persisters can survive antibiotic treatment by entering a metabolically-dormant state[2, 19, 20]. Persister cells do not typically carry genetic mutations but rather exhibit phenotypic resistance to antibiotics[21]. In Escherichia coli, the fraction of a population which represents persister cells increases dramatically in late-exponential and stationary phases. Chromosomally-encoded toxins may be important contributors to the persister phenotype but the underlying mechanisms that control the stochastic persistence phenomena are not well understood[22-25]. Persisters constitute a reservoir of latent cells that can begin to regrow once antibiotic treatment ceases and may be responsible for the increased antibiotic tolerance observed in bacterial biofilms[20]. By surviving treatment, persisters may play an important role in the development of mutations or acquisition of genes that confer antibiotic resistance.

Several strategies have been proposed for controlling antibiotic resistant infections. New classes of antibiotics would improve the arsenal of drugs available to fight antibiotic-resistant bacteria but few are in pharmaceutical pipelines[3, 26]. Surveillance and containment measures have been instituted in government and hospitals so that problematic infections are rapidly detected and isolated but do not address the fundamental evolution of resistance[12]. Cycling antibiotics is one method of controlling resistant organisms but is costly and may not be efficacious[27, 28]. Reducing the over-prescribing of antibiotics has only moderately reduced antibiotic resistance[29]. Efforts have been also made to lessen the use of antibiotics in farming but some use is inevitable[30].

Using bacteriophage to kill bacteria has been in practice since the early 20th century, particularly in Eastern Europe[16, 17]. Bacteriophage can be chosen to lyse and kill bacteria or can be modified to express lethal genes to cause cell death[31-35]. However, bacteriophage which are directly lethal to their bacterial hosts can also produce phage-resistant bacteria in short amounts of time[6, 7, 31, 32, 36]. In addition to the aforementioned approaches, novel methods for designing antimicrobial drugs are becoming more important to extending the lifespan of the antibiotic era[37]. Combination therapy with different antibiotics or antibiotics with phage may enhance bacterial cell killing and thus reduce the incidence of antibiotic resistance, and reduce persisters[38-41]. Unmodified filamentous bacteriophage have been shown to augment antibiotic efficacy[42]. Systems biology analysis can be employed to identify pathways to target and followed by synthetic biology to devise methods to attack those pathways[38, 43, 44].

Bacterial biofilms are sources of contamination that are difficult to eliminate in a variety of industrial, environmental and clinical settings. Biofilms are polymer structures secreted by bacteria to protect bacteria from various environmental attacks, and thus result also in protection of the bacteria from disinfectants and antibiotics. Biofilms may be found on any environmental surface where sufficient moisture and nutrients are present. Bacterial biofilms are associated with many human and animal health and environmental problems. For instance, bacteria form biofilms on implanted medical devices, e.g., catheters, heart valves, joint replacements, and damaged tissue, such as the lungs of cystic fibrosis patients[97]. Bacteria in biofilms are highly resistant to antibiotics and host defenses and consequently are persistent sources of infection[98].

Biofilms also contaminate surfaces such as water pipes and the like, and also render other industrial surfaces hard to disinfect[97]. For example, catheters, in particular central venous catheters (CVCs), are one of the most frequently used tools for the treatment of patients with chronic or critical illnesses and are inserted in more than 20 million hospital patients in the USA each year. Their use is often severely compromised as a result of bacterial biofilm infection which is associated with significant mortality and increased costs. Catheters are associated with infection by many biofilm forming organisms such as *Staphylococcus epidermidis, Staphylococcus aureus, Pseudomonas aeruginosa, Enterococcus faecalis* and *Candida albicans* which frequently result in generalized blood stream infection. Approximately 250,000 cases of CVC-associated bloodstream infections occur in the US each year with an associated mortality of 12%-25% and an estimated cost of treatment per episode of approximately $25,000. Treatment of CVC-associated infections with conventional antimicrobial agents alone is frequently unsuccessful due to the extremely high tolerance of biofilms to these agents. Once CVCs become infected the most effective treatment still involves removal of the catheter, where possible, and the treatment of any surrounding tissue or systemic infection using antimicrobial agents. This is a costly and risky procedure and re-infection can quickly occur upon replacement of the catheter.

SUMMARY OF THE INVENTION

Described herein are methods and compositions for the detection of target genes. The methods and compositions described herein can be used to detect cells expressing any target gene, such as bacterial genes, viral genes, etc., but are particularly well suited for the detection of, for example drug resistance genes (e.g., antibiotic resistance) in bacteria, or multi-drug resistance transporter genes in eukaryotic cells. The methods and compositions described herein further permit the selective expression of an effector gene in those cells expressing the target gene. In this manner, cells expressing a target gene can be selectively targeted for treatment or elimination. In certain aspects, the methods and compositions described herein permit the selective expression of an agent such as a therapeutic gene product, in a specifically targeted population of cells in an organism.

The inventors have developed a synthetic nucleic acid sensor-effector gene circuit. In cells without a target gene, the circuit suppresses e.g., effector production, but in the presence of the target gene the suppression is subject to competition, such that the synthetic sensor is de-repressed and permits expression of the effector gene. As discussed in further detail below, preferred embodiments relate to the expression of a reporter that permits identification of a cell or a cell-type expressing a target gene. Such embodiments, permit the detection or discrimination of cells expressing a given target gene and can be applied to detect, for example, viral, fungal or bacterial infection or contamination, as well as the presence of cells with specific traits, e.g., drug or antibiotic resistance.

One aspect disclosed herein relates to a method of detecting a cell expressing a target gene by introducing to the cell a nucleic acid construct encoding a portion of the target gene sequence fused to an effector gene sequence (herein referred to as the 'sensor construct'), and a construct encoding an inhibitory nucleic acid sequence directed against that portion of the target gene sequence, wherein in the absence of the target gene the inhibitory nucleic acid sequence suppresses effector gene expression. Detection of the target gene involves monitoring expression of the effector gene sequence in the cell and comparing the level of effector gene sequence expression to a reference level, wherein if expression of the effector gene sequence is increased relative to the reference level, the target gene is detected in the cell.

In one embodiment of this aspect and other aspects disclosed herein, the target gene is a mutant gene.

In another embodiment of this aspect and other aspects described herein, the nucleic acid construct encoding a portion of the target gene sequence fused to an effector gene sequence and the construct encoding an inhibitory nucleic acid sequence are encoded on the same nucleic acid molecule.

In another embodiment of this aspect and other aspects disclosed herein, the cell type is bacterial and the target gene is a drug resistance or virulence gene. Alternatively, the cell type is eukaryotic/mammalian.

In another embodiment of this aspect and other aspects described herein the target gene is a viral gene or a multi-drug resistance transporter gene.

In another embodiment of this aspect and other aspects described herein, the target gene is an oncogene or tumor associated gene. In another embodiment of this aspect and other aspects described herein, the effector gene sequence encodes a reporter molecule and comprises a detectable polypeptide, for example an enzyme, a fluorescent polypeptide, a luminescent polypeptide or an antigen. The fluorescent polypeptide can be selected, for example, from the group consisting of GFP, YFP, EGFP, EYFP EBFB, and fluorescent variants thereof.

Also disclosed is an engineered gene sensor comprising a nucleic acid sequence encoding a portion of a target gene sequence fused to an effector gene sequence (herein referred to as 'sensor construct') and further comprising a construct encoding an inhibitory nucleic acid sequence directed against a portion of the target gene sequence, wherein the presence of target gene expression in a cell permits the effector gene expression to produce an effector polypeptide which mediates delivery of an agent or mediates cell killing.

Also disclosed is a method for selectively killing a cell expressing a target gene, the method comprising the steps of introducing to the cell a nucleic acid construct encoding a portion of the target gene sequence fused to an effector gene sequence, and a construct encoding an inhibitory nucleic acid sequence directed against a portion of the target gene sequence, wherein in the absence of target gene expression the inhibitory nucleic acid sequence suppresses expression of the effect gene; wherein the presence of target gene expression in the cell permits effector gene expression to produce an effector polypeptide, and wherein expression of the effector polypeptide mediates cell killing.

In one embodiment, the effector gene sequence encodes a polypeptide that mediates cell killing. As non-limiting examples, the effector gene sequence can encode a hok or CcdB polypeptide in a bacterial cell. Alternatively, the effector gene sequence can be selected from, for example apoptotic gene products, or anti-angiogenic gene products. In another embodiment, the effector gene encodes for an RNA interference molecule.

Another aspect of the invention disclosed herein is a system for detecting a target gene, the system comprising a nucleic acid construct encoding a portion of the target gene sequence fused to an effector gene sequence (sensor construct); and a construct encoding an inhibitory nucleic acid sequence that inhibits the sensor construct expression, wherein both nucleic acid constructs are comprised by the same nucleic acid molecule. In one embodiment, the nucleic acid molecule comprises a vector, for example a plasmid vector, a viral vector or a bacterial vector. In one embodiment, the effector gene sequence encodes a polypeptide that mediates cell killing. Alternatively, the effector gene sequence can encode an RNA interference molecule, which may or may not mediate cell killing. In one embodiment the effector is an apoptotic gene, for example a caspase. In another embodiment, the effector alters angiogenic pathways and expression of angiogenic genes (e.g., VEGF, PDGF, FGF and Akt). In another embodiment, the effector gene encodes a detectable protein such as a fluorescent protein.

Another aspect of the invention relates to a kit for detecting a target gene, the system comprising (a) a nucleic acid construct encoding a portion of the target gene sequence fused to an effector gene sequence, (b) a construct encoding an inhibitory nucleic acid sequence that inhibits the expression of the target gene portion/effector fusion, wherein the nucleic acid constructs of (a) and (b) are comprised by the same nucleic acid molecule and (c) packaging materials therefor.

DEFINITIONS

As used herein, the term 'portion' when used in relation to a target gene sequence denotes a length of nucleic acid sequence sufficient to mediate inhibition by an inhibitory nucleic acid sequence as described herein.

As used herein, the term 'effector' designates a nucleic acid sequence encoding a polypeptide or RNA interference molecule, which upon expression produces a reporter protein, a therapeutic agent or mediates cell killing.

As used herein, the terms 'inhibits', 'inhibiting' and 'inhibition' signify a reduction in a measurable parameter (e.g., mRNA or protein level) of target gene expression by at least 10%, e.g., at least 15%, at least 20%, at least 30%, at least 40%, at least 50%, at least 60%, at least 70%, at least 80%, at least 90%, at least 95%, at least 99% or even 100% (ie target gene expression is inhibited completely), relative to a reference.

As used herein, the terms 'suppresses', 'suppressing' and 'suppression' denote maintenance of effector gene expression at levels that are within 10% of reference levels. 'Reference levels' denotes a measure of reporter gene expression compared to a reference. The term 'Reference' as described herein denotes a cell which does not express the target gene and represents the baseline level of reporter gene or effector gene expression, e.g., in a cell containing a sensor construct and an inhibitory construct as described herein.

As used herein, the term 'increased' when used in relation to gene expression or another measurable parameter means detection of e.g., effector gene expression at levels at least 10% higher than reference levels, e.g., at least 20%, at least 30%, at least 40%, at least 50%, at least 60%, at least 70%, at least 80%, at least 90%, at least 100%, at least 2-fold, at least 5-fold, at least 10-fold, at least 100-fold or more.

As used herein, the term 'drug-resistance gene' denotes a gene which upon expression allows cells to survive in the presence of a drug which is toxic to cells lacking expression of the gene.

As used herein, the term 'virulence gene' signifies a gene which upon expression renders a cell more pathogenic than its counterparts which lack expression of the virulence gene.

As used herein, the term 'tumor associated gene' refers to a gene which upon expression produces a tumor antigen in tumorogenic cells. The term 'tumor antigen' is used herein to refer to proteins present only on tumor cells (tumor specific antigens) as well as those present on normal cells but expressed preferentially on tumor cells (tumor associated antigens).

As used herein, the term "mutant gene" refers to a gene that differs from a wild-type gene in sequence or function. A "mutant gene" will generally result in a protein or polypeptide that differs by at least one amino acid relative to a wild-type reference sequence, and can encompass differences in, for example, at least two, at least three, at least four, at least five, at least 10 amino acids, etc. relative to a reference sequence. A "mutant gene" will generally, but not always, exhibit altered function relative to a wild-type gene. For example, the product of a mutant gene can exhibit enhanced (e.g., by at least 5%, at least 10%, at least 15%, at least 20%, at least 30%, at least 40%, at least 50%, at least 1 fold, at least 2 fold, or more) or decreased (e.g., by at least 5%, at least 10%, at least 15%, at least 20%, at least 30%, at least 40%, at least 50%, at least 60%, at least 70%, at least 80%, at least 90% or more, including 100%, (i.e., no function) function relative to a wild-type gene. The term "mutant gene" also encompasses a gene which encodes a wild-type polypeptide but which, due to a change in a regulatory sequence, is expressed (or not expressed) inappropriately, e.g., at least 20% higher or lower, at least 30% higher or lower, at least 40% higher or lower, at least 50% higher or lower, at least 60% higher or lower, at least 70% higher or lower, at least 80% higher or lower or at least 90% higher or lower than the wild type gene.

As used herein, the term 'selectively killing' means a given treatment or process which results in the killing of cells expressing a target gene to the substantial exclusion of cells that do not express the target gene. 'Substantial exclusion' as used in this context means that ≤30% of cells killed did not express the target gene, or alternatively, that ≤25%, ≤20%, ≤15%, or ≤10% of cells killed did not express the target gene, preferably ≤5% of cells killed did not express the target gene; more preferably ≤1%.

As used herein, the term 'mediates cell killing' denotes the production of an effector that promotes cell death by increasing susceptibility of cells to drug treatments, activation of an endogenous cell death pathway, suppression of an endogenous growth pathway, or an effector that is directly toxic to the cell e.g., the bacterial toxin MazF; an effector that mediates cell killing can be a polypeptide or in other instances a nucleic acid, for example an RNA interference molecule.

An "RNA interference molecule" as used herein, is defined as any agent which interferes with or inhibits expression of a target gene or genomic sequence by RNA interference (RNAi). Such RNA interfering agents include, but are not limited to, nucleic acid molecules including RNA molecules which are homologous to the target gene or genomic sequence, or a fragment thereof, short interfering RNA (siRNA), short hairpin or small hairpin RNA (shRNA), microRNA (miRNA) and small molecules which interfere with or inhibit expression of a target gene by RNA interference (RNAi).

"RNA interference (RNAi)" is an evolutionarily conserved process whereby the expression or introduction of RNA of a sequence that is identical or highly similar to a target gene results in the sequence specific degradation or specific post-transcriptional gene silencing (PTGS) of messenger RNA (mRNA) transcribed from that targeted gene[45], thereby inhibiting expression of the target gene. In one embodiment, the RNA is double stranded RNA (dsRNA). This process has been described in plants, invertebrates, and mammalian cells. In nature, RNAi is initiated by the dsRNA-specific endonuclease Dicer, which promotes processive cleavage of long dsRNA into double-stranded fragments termed siRNAs. siRNAs are incorporated into a protein complex (termed "RNA induced silencing complex," or "RISC") that recognizes and cleaves target mRNAs. RNAi can also be initiated by introducing nucleic acid molecules, e.g., synthetic siRNAs or RNA interfering agents, to inhibit or silence the expression of target genes. As used herein, "inhibition of target gene expression" includes any decrease in expression or protein activity or level of the target gene or protein encoded by the target gene as compared to a situation wherein no RNA interference has been induced. The decrease will be of at least 10%, 20%, 30%, 40%, 50%, 60%, 70%, 80%, 90%, 95% or 99% or more as compared to the expression of a target gene or the activity or level of the protein encoded by a target gene which has not been targeted by an RNA interference molecule. The terms "RNA interference" and "RNA interference molecule" as they are used herein are intended to encompass those forms of gene silencing mediated by double-stranded RNA, regardless of whether the RNA interfering agent comprises an siRNA, miRNA, shRNA or other double-stranded RNA molecule.

"Short interfering RNA" (siRNA), also referred to herein as "small interfering RNA" is defined as an RNA agent which functions to inhibit expression of a target gene, e.g., by RNAi. An siRNA may be chemically synthesized, may be produced by in vitro transcription, or may be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, 22, or 23 nucleotides in length, and may contain a 3' and/or 5' overhang on each strand having a length of about 0, 1, 2, 3, 4, or 5 nucleotides. The length of the overhang is independent between the two strands, i.e., the length of the overhang on one strand is not dependent on the length of the overhang on the second strand. Preferably the siRNA is capable of promoting RNA interference through degradation or specific post-transcriptional gene silencing (PTGS) of the target messenger RNA (mRNA).

As used herein, the term 'alters' denotes an increase or decrease in effector gene expression of at least 10% e.g., at least 15%, at least 20%, at least 30%, at least 40%, at least 50%, at least 60%, at least 70%, at least 80%, at least 90%, at least 95%, at least 99% or even 100% or more. Where the alteration is a decrease 100% means complete or substantially complete inhibition of effector gene expression. By 'substantially complete inhibition' is meant that expression is not detected above background by standard methods. Where the alteration is an increase the term further encompasses greater than 100% increase, e.g., 2-fold, 5-fold, 10-fold, 100-fold or further increase over a baseline or reference level.

BRIEF DESCRIPTION OF THE FIGURES

FIG. 6. Example nucleic acid sequences that encode for bacterial antibiotic resistance. Chloramphenicol acetyltransferase, SEQ ID NO: 2; Tetracycline resistance sequence, SEQ ID NO: 3; kanamycin resistance sequence, SEQ ID NO: 4; ampicillin resistance sequence, SEQ ID NO: 5; vancomycin resistance genes vanA (SEQ ID NO: 6), vanH (SEQ ID NO: 7) and vanX (SEQ ID NO: 8); and methicillin resistance (SEQ ID NO: 9).

Figure 1:
FIG. 1. A schematic depiction of the paired-termini design which extends the half-life of an inhibitory nucleic acid sequence upon introduction to a cell[46] (Incorporated from reference quoted herein). The nucleic acid sequence depicted is SEQ ID NO: 1.

Table 1 includes the nucleic acid sequence (SEQ ID NO: 10) of an exemplary gene sensor comprising a nucleic acid vector used herein and illustrates the sequence of the pZE21s1-cat plasmid. The PT7 antisense stem loop structure is illustrated by bold and underlined letters. DNA coding for the antisense RNA to cat is denoted with italics and large case letters. The DNA sequence for the cat-gfp fusion polypeptide is denoted by italics/lowercase letters and underlined large case letters, respectively.

Table 2 includes a list of potential target genes involved in enhanced virulence of bacteria.

DETAILED DESCRIPTION

Described herein are methods and compositions for the detection of target genes. The methods and compositions described can be used to detect cells expressing any target gene, but are particularly well suited for the detection of, for example drug resistance genes (e.g., antibiotic resistance) in bacteria, or multi-drug resistance transporter genes in eukaryotic cells. The methods and compositions described herein further permit the selective expression of an effector gene in those cells expressing the target gene. In this manner, cells expressing a target gene can be selectively targeted for treatment or elimination. In certain aspects, the methods and compositions described herein permit the selective expression of an agent such as a therapeutic gene product, in a specifically targeted population of cells in an organism.

The following describes materials and methods useful for the practice of the invention described herein.

Gene Sensor System

The gene sensor described herein comprises a nucleic acid vector, which encodes for (a) a portion of the target gene, fused to an effector gene sequence (sensor construct); and (b) an inhibitory nucleic acid molecule directed against the sensor construct. Together these two sequences form a gene sensor coupled to an effector molecule. Upon expression of the sensor construct and the inhibitory nucleic acid molecule in the same cell, the target gene portion of the sensor construct transcript binds to the inhibitory nucleic acid sequence. This binding suppresses expression of the effector gene portion of the sensor construct and retains effector molecule expression at a level comparable to the reference or control level. However, if the target gene is also expressed in the cell, the mRNA sequence encoding the target gene product competes with the sensor construct transcript for binding to the inhibitory nucleic acid molecule. As the system approaches equilibrium, the target gene mRNA will displace the sensor construct transcript from the inhibitory nucleic acid molecule. Displacement of the sensor construct transcript releases the inhibition of the effector portion of the sensor construct, thereby allowing expression of the selected effector molecule.

The effector molecule can produce a reporter molecule that would be useful for detection of cells in a population that express the target gene. The reporter molecule can mediate fluorescence, a colorimetric signal or confer resistance to a drug to allow one to distinguish cells expressing the target gene from cells lacking expression.

Alternatively, the effector can selectively mediate cell killing. The effector can encode for a polypeptide toxic to the cell or a polypeptide that activates cell death pathways (e.g., apoptotic death pathways) or interferes with cell growth pathways (e.g., angiogenic pathways). Effector genes can include, for example caspases or FLK(VEGF trap) or any of those described herein below.

Figure 2:
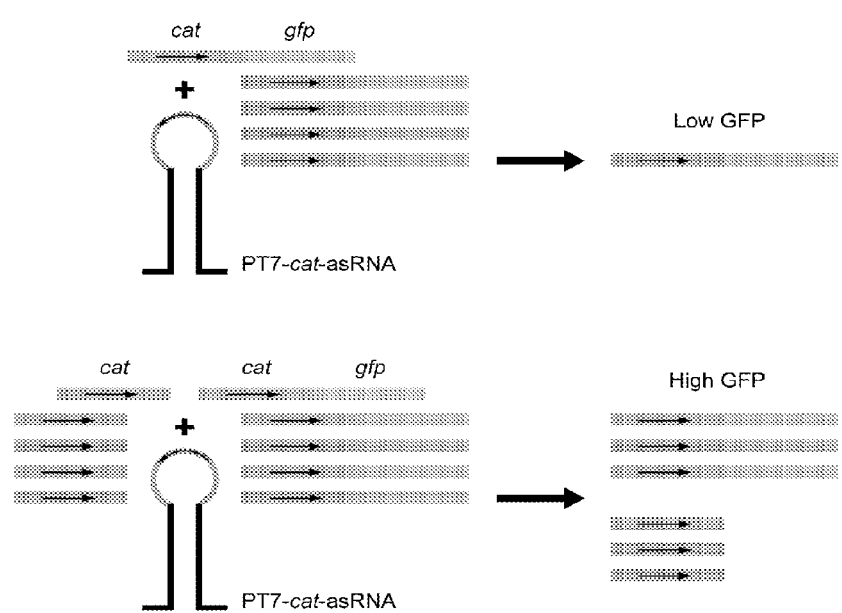
FIG. 2. A diagram depicting the expression of a reporter molecule (e.g., GFP) in the absence and presence of a target gene.
Figure 3:
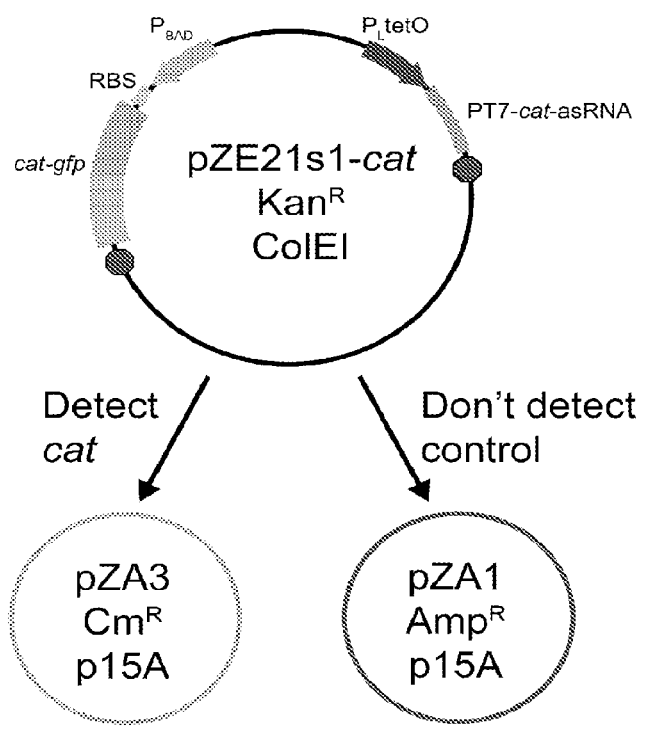
FIG. 3. A schematic diagram depicting an engineered gene sensor design which allows the detection of a target gene but not other genes expressed in the cell.

FIG. 1 depicts one example of an inhibitory nucleic acid sequence in the form of an antisense RNA directed against the target gene. In this example, paired termini technology[46] is used to extend the half-life of inhibition in the cell. The antisense RNA in this example is directed against the target gene transcript but also binds to the target gene portion of the sensor construct transcript. FIG. 2 is a schematic depiction of expression of an exemplary reporter molecule (GFP) in the absence and presence of target gene expression in a cell. In the absence of the target gene transcript the sensor construct transcript is inhibited by binding of its transcript to the inhibitory nucleic acid construct. Upon target gene expression, the encoding mRNA competes with the target gene portion of the sensor construct transcript for binding to the inhibitory nucleic acid transcript. This displacement of the sensor construct transcript permits the effector gene to be expressed and in this embodiment the fluorescence of GFP can be detected as a read out of target gene expression. It is important to note that the inhibitory nucleic acid molecule need not necessarily be an antisense molecule. It could also be, for example, an RNA interference-type molecule that mediates silencing of expression of the sensor construct, e.g., by cleavage of the sensor construct's RNA transcript in, for example a eukaryotic cell. Ribozymes specific for a portion of a target gene transcript are also contemplated.

Target Genes

One aspect of the present invention is detection of a target gene in a cell. Any gene can be a target gene. A target gene is preferably a gene of interest to allow detection and optionally subsequent treatment of disease. In one embodiment the target gene is a mutant gene. This aspect of the invention allows flexibility in the choice of target to extend the application to various disease states.

A target gene is selected based on the genetic characteristics of the cell to be detected (e.g., bacterial vs. eukaryotic/mammalian), the disease to be detected or treated (e.g., antibiotic resistant bacterial infections, cancer) or a disease related to the lack of or excess of one or more protein targets (e.g., Cystic Fibrosis, Adrenoleukodystrophy). For example, in the treatment of an antibiotic-resistant bacterial infection, a target gene that confers resistance to a particular agent would be selected in order to allow detection of antibiotic resistant cells in a population. Some examples of target genes which confer antibiotic resistance to bacteria comprise β-lactamase genes, penicillin binding site (PBP) genes, and multi-drug efflux pump genes (e.g., members of the RND, MFS, SMR and MATE families of multi-drug efflux pumps; specific examples include but are not limited to MExAB-OprM, MexCD-OprJ, MexEF-OprN, MesHI-OprD, MexJK-OprM, MexXY-OprM, AdeABC, SmeABC, SmEDEG, CeoAB-OpcM, AmrAB-AprA, AcrAB-TolC, MepA, EmeA, Lsa and PmrA)[48]. Other non-limiting examples of antibiotic resistance genes include LmrA, AcrB, AcrA, TolC, Sav1866, EmrE, EmrD, LmrP, BmrR, VanS, VanR, VncS, VncR, RprX, RprY, cat, TetR, kan, bla, vanA/vanH/vanX, mecR, vanB/vanH/vanX, qnr, McbG, ermB, ermC, ermG, and QacR. (For support see [49-54])

Another example of a target gene in bacteria is a virulence gene, which upon expression can confer increased pathogenicity of a cell population. By "increased" in this context is meant at least 10%, at least 20%, at least 30%, at least 40%, at least 50%, at least 60%, at least 70%, at least 80%, at least 90%, at least 2 fold, at least 5-fold or more increased relative to the pathogenicity of a reference pathogen, e.g., a pathogen that differs from the subject pathogen essentially only in lacking that virulence gene. Virulence genes produce factors which increase the ability of bacteria to induce illness in its host. Increased virulence can result from the following: (a) the enhanced expression of adhesion molecules that allow host uptake of bacteria, (b) the production of proteins that allow bacteria to survive in hostile environments (e.g., extreme pH of the gastrointestinal system), (c) the ability to disrupt host cell membranes to increase speed of invasion, (d) the production of host immune-suppressive proteins, and (e) the production of toxins secreted by bacteria that can cause tissue damage. Some non-limiting examples of virulence genes in bacteria are shown in Table 2 and can be found, for example on the world wide web at jenner.ac.uk/BacBix3/PPprints.htm.

Other non-limiting examples of virulence gene targets, but are not limited, to FimC, FimD, FimH, PapC, PapD, PapG, PrsD, PrsC, PrsG, SfaE, SfaF, SfaS, HifB, HifC, HifE, FimB, PefD, PefC, LpfB, LpfC, MrkB, MrkC, MyfB, MyfC, MrkD, CooB, CooC, CooD, CsgA, CsgB, CsgE, CsgF, CsgG, AgfB, AgfA, PilC, pilin, AgrC, AgrA, AlgD, AlgR, RcsC, RcsB, BvgS, BvgA, PhoQ, and PhoP[52,55]. Alternatively, a target gene can be a gene expressed by a eukaryotic/mammalian cell. An example of this embodiment includes the target genes expressed by cancerous tumors, wherein the target gene is, for example, a mutant gene which confers drug resistance or a proliferative advantage to a particular cell population. For example, the mammalian P-glycoprotein, also known as ABCB1, is an active transporter that pumps a variety of toxic agents used in chemotherapy out of the cell. Inhibition of mammalian P-glycoprotein could confer increased sensitivity of tumors to existing chemotherapeutic agents. The target could alternatively be a tumor antigen or tumor associated antigen that permits targeting of cells expressing them with a therapeutic molecule. Other non-limiting examples of tumor associated genes include, for example, those described in U.S. Pat. No. 6,635,476, which is incorporated herein by reference[56]. Examples include but are not limited to alfa-fetoprotein (AFP), C-reactive protein (CRP), cancer antigen-50 (CA-50), cancer antigen-125 (CA-125) associated with ovarian cancer, cancer antigen 15-3 (CA15-3) associated with breast cancer, cancer antigen-19 (CA-19) and cancer antigen-242 associated with gastrointestinal cancers, carcinoembryonic antigen (CEA), carcinoma associated antigen (CAA), chromogranin A, epithelial mucin antigen (MC5), human epithelium specific antigen (HEA), Lewis(a)antigen, melanoma antigen, melanoma associated antigens 100, 25, and 150, mucin-like carcinoma-associated antigen, multidrug resistance related protein (MRPm6), multidrug resistance related protein (MRP41), Neu oncogene protein (C-erbB-2), neuron specific enolase (NSE), P-glycoprotein (mdr1 gene product), multidrug-resistance-related antigen, p170, multidrug-resistance-related antigen, prostate specific antigen (PSA), CD56, and NCAM. Further non-limiting examples of oncogene target genes include those described by Croce, 2008, *New England Journal of Medicine,* 358:502-511 (and in the Supplementary data of the same), which is incorporated herein by reference[57]. Examples include but are not limited to ERBB2, EGFR, VEGF, ABL, PDFR, KIT, FLT3, MYC, RAS, BCL2, v-myc, N-MYC, L-MYC, v-myb, v-fos, v-jun, v-ski, v-rel, v-ets-1, v-ets-2, v-erbA1, v-erbA2, MDM2, ALL1, v-sis, int2, KS3, HST, v-fms, v-KIT, v-ros, MET, TRK, RET, mas, SRC, v-yes, v-fgr, v-fes, ABL, H-RAS, K-RAS, N-RAS, BRAF, gsp, gip, Dbl, Vav, v-mos, v-raf, pim-1, v-crk and c-MYC.

Another example of target gene detection in eukaryotic cells relates to latent viral infections, which persist due to the virus' ability to remain dormant in a cell it has infected or its ability to incorporate its viral genome into the eukaryotic genome of the cell. Example infections include herpes simplex virus, Human Immunodeficiency Virus (HIV), Epstein-barr virus, Varicella-zoster virus and human papilloma virus among others. Examples of target genes involved in herpes simplex virus latency in neurons include, but are not limited to, immediate early gene (IE), latency associated transcripts (LATS), and histone deacetylases (HDACs). Some non-limiting examples of HIV latent genes in CD4+ T-cells include APO-BEC3G, CCR5, HDACs, Sp1, LEF-1, COUP-TF, YYI, ETS-1, USF, NF-kB, AP-1, NFAT, tat, rev, nev and P-TEFb. Other genes related to viral latency are known to those skilled in the art. (For further support please see [58-61])

Effectors

Disclosed herein are methods for detecting target genes that involve the subsequent activation of effector gene sequences. Effector genes encode for polypeptides with a desired function in the cell. Frequently, an effector will be exogenous to the cell in which it is expressed. However, it is also contemplated that an effector, in some situations, may be an endogenous polypeptide expressed, for example at a higher level in the host cell.

In one embodiment, the effector gene sequence encodes for a reporter molecule that is expressed in the presence of a target gene to allow detection of cells in a population that carry the target gene. A reporter is encoded by a molecule that can be attached to a nucleic acid of interest (e.g., a portion of the target gene) that allows the expression of the nucleic acid to be easily identified and/or quantified in a cell. In addition, reporter molecules can also be used for selectively identifying cells in a population by e.g., allowing for growth on a medium or in the presence of an agent that would normally not permit growth of the cell population. A reporter molecule can allow the user to determine if the sensor construct is being expressed in the cell and in some cases can be used to quantify the level of expression compared to a reference level. Reporters can be enzymes which produce light (e.g., luciferase), colored products (e.g., β-galactosidase), or confer antibiotic resistance (e.g., CAT). Reporters can be enzymes that catalyze any reaction that yields a detectable product when acting on a substrate. In addition, reporters can also be antigens that are detected by binding to specific antibodies using standard methods (e.g., FACS, Western blotting, dot blotting, immunohistochemistry or ELISA). Reporters can also be fluorescent polypeptides that upon stimulation with a certain wavelength of light, will emit fluorescence at a separate wavelength (e.g., GFP and other fluorescent variants described herein).

In addition to detection where the effector is a reporter, another embodiment relates to the selective killing of cells mediated by effector gene sequences. In this manner, gene sensors as described herein allow detection of cells expressing a target gene and couples this detection to the production of a polypeptide that mediates cell killing. The mediation of cell killing can be direct, such that the effector encodes for expression of a toxin, or indirect, for example by making a cell more susceptible to an agent or drug.

The mediation of cell killing in bacteria can occur by influencing bacterial programmed cell death pathways that exist in the form of a toxin/antitoxin pair. The toxin is inactivated by antitoxin sequestration under normal growth conditions. However, some cellular stresses (e.g., thymine starvation or antibiotic treatment) can cause the loss of the antitoxin protein, thereby releasing the toxin. The toxin initiates an irreversible cell death cascade by virtue of its endoribonucleolytic effect (e.g., cleavage) on mRNA molecules. The genes involved in the toxin/anti-toxin pair are good candidates for the choice of effector in the described system and effectors can include, but are not limited to the toxins mazF, ccdB, relE, parE, higB, doc, or vapC, or the inhibition of anti-toxin genes such as masE, skfE, skfF, relB, parD, higA, phd, and vapB. (Support for this concept is provided by [62,63])

The mediation of mammalian cell killing by the effector can also result from activation of a cell death pathway. Currently there are three known types of programmed cell death in mammalian cells: (a) apoptosis, (b) necrosis, and (3) autophagy. While the activation of any of these pathways would mediate cell killing, it is preferable to utilize a member of the apoptotic cell death pathway since it remains the most highly characterized. Apoptosis can result from two different activation pathways, termed the 'extrinsic or death receptor pathway' and 'intrinsic or stress pathway'. The extrinsic pathway is activated by extracellular stimuli that bind to surface receptors (e.g., TRAIL receptor), whereas the intrinsic pathway responds to intracellular stimuli (e.g., mitochondrial membrane permeabilization or cytochrome c release). Both pathways converge downstream and promote activation of the caspase family of proteases. Active caspases proteolytically cleave hundreds of intracellular proteins involved in cell survival, DNA repair and replication of the cell. Thus, for example caspases, especially the initiator caspases such as caspase-2, caspase-8, caspase-9, and caspase-10 are appropriate for use as an effector in this system.

There exists a balance of anti-apoptotic and apoptotic stimuli in a cell at any given time. Therefore, apoptosis can be influenced either by activating a pro-apoptotic pathway or by inhibiting an anti-apoptotic pathway. Activation can occur, for example, by the effector expressing a pro-apoptotic gene or by inhibiting an anti-apoptotic gene, e.g., by RNA interference, or by intracellular expression of an antibody fragment or binding partner that inactivates the anti-apoptotic gene or its product. For example, the Bcl-2 family of proteins contain pro-apoptotic proteins such as Bax and Bak, which promote cytochrome c release from mitochondria. Activation of Bax and Bak can mediate cell death by apoptosis. Alternatively, the Bcl-2 family also includes anti-apoptotic members including Bcl-2, Bcl-xL, Bcl-w, Mcl-1 and A1, which can be inhibited by the use of an appropriate effector in the system described herein. Similarly, members of the 'inhibitor of apoptosis' (IAP) family including, but not limited to, DIAP, XIAP, Smac/Diablo, Omi/HtrA2, GSPT1/eRF3, and cIAP are potential effector targets that could be inhibited in cells e.g., by RNA interference. Other options of effectors from the extrinsic or death receptor pathway include, but are not limited to death receptors (e.g., TRAIL receptor), Fas activated death domain (FADD), and caspase 8. Some further non-limiting examples of the intrinsic/stress pathway include BH3 domain containing proteins (specific examples include BIM, BID, PUMA, BAD, HRK, BIK and NOXA), Apaf1, caspase-3, caspase-6, and caspase-7. (For further support please see [64,65])

In another embodiment, the effector gene sequence can be used to replace a polypeptide that is missing in a cell. For example, the absence of the chloride channel CFTR is responsible for the manifestation of cystic fibrosis and could be replaced using the technology described herein. An alternative example is the absence of the ABC transporter isoform D1, which manifests as adrenoleukodystrophy. Thus ABCD1 is another possible effector for use in this system. Any other defective or mutant protein could potentially be replaced using this approach. An advantage of this approach is that it can specifically target cells expressing the mutant gene for replacement of the corrective gene product.

In an alternative embodiment, the effector gene sequence can encode for a repressor of a polypeptide. For example, a repressor can be designed as described by Bartsevich et al, 2000 *Molecular Pharmacology* 58:1-10 incorporated herein by reference [66], which for example would mediate the selective repression of a multi-drug resistance tranporter. Similarly, the effector gene sequence can encode for a transcription factor that will repress the production of polypeptides, for example those involved in drug resistance in both bacterial and mammalian cells. This repression can be a result of enhanced production of antisense RNA, siRNA, shRNA, or miRNA by the transcription factor that will produce inhibition of target expression. For further support on siRNA and shRNA strategies see, for example de Fougerolles, A., et al (2007); and Xiang, S. et al (2006), which are incorporated herein by reference [67,68])

In another embodiment the effector gene sequence encodes for an RNA interference molecule that can inhibit or activate any of a number of desired cell pathways, for example, cellular growth, angiogenic or apoptotic pathways.

In another embodiment the effector gene sequence can encode for e.g., porins that enhance antibiotic removal from the cell as described by Ceccarelli et al, 2004[54].

In another embodiment the effector gene sequence can encode factors that increase death or susceptibility to e.g., antibiotics[69-71].

In another embodiment the effector gene sequence can encode for e.g., a soluble receptor or antibody that binds to and inhibits a target gene polypeptide.

Preparation of a Sensor Construct System

The target gene of interest and the effector gene sequence are chosen based on a rational approach designed to target a specific cell or disease state. Most often, a portion of the target gene transcript comprising a minimum of 10 base pairs to a maximum length of the entire target gene sequence is ligated to the effector gene sequence such that the target gene sequence and effector gene sequence form a seamless polypeptide. It is important to choose a portion of target gene sequence for the sensor construct that is not capable of producing a functional target protein from the sensor construct. In order to prevent functional target protein expression from the sensor construct, it is preferable to use a smaller, e.g., incomplete, portion of the target gene to fuse to the effector sequence. Other approaches to prevent functional protein expression by the sensor construct involve altering the nucleic acid sequence of the target gene portion of the sensor construct and include, but are not limited to, the insertion or loss of a base pair to produce a non-coding frame shift, mutation of essential domains (e.g., ATP binding domains of kinases), or production of a missense polypeptide. It is also important to note that the portion of the target gene transcript does not have to be identical in sequence to the target gene and can instead have a degree of mismatch. This degree of mismatch can be altered as desired in the design of the sensor construct in order to change binding characteristics as described herein (see 'Mediation of inhibition' and 'RNA interference section').

The other molecule of the gene sensor, termed the inhibitory nucleic acid construct, can also be tailored to the needs of the user and choice of the target gene. The inhibitory nucleic acid sequence utilized to bind the sensor construct is determined by, for example, the species of cell to be targeted. Bacterial cells rapidly degrade foreign nucleic acids, so in order to extend the half-life of the inhibitory nucleic acid transcript sequence in the cell, the construct is inserted, for example, into a paired termini system described by Nakashima et al[46]. The inhibitory nucleic acid sequence can be inserted, for example, by ligation into the paired termini design[46] at the top of the stem. The inhibitory nucleic acid sequence can be more flexible in mammalian cells, which permits the use of RNA interference molecules, e.g., siRNA, shRNA, and miRNA.

In one embodiment, the inhibitory nucleic acid sequence as well as the target gene-effector gene sequence encoding for the fusion polypeptide are encoded on the same nucleic acid molecule. In an alternative embodiment, the inhibitory nucleic acid sequence as well as the target gene-effector gene sequence encoding for the fusion polypeptide are encoded on two separate nucleic acid molecules, allowing for greater sensitivity of detection. The use of two constructs permits the changes in effector concentration to be regulated tightly by altering the dose of the inhibitory nucleic acid molecule and the sensor construct in relation to each other.

RNA Interference

RNA interference (RNAi) is an evolutionarily conserved process whereby the expression or introduction of RNA of a sequence that is identical or highly similar to a target gene results in the sequence specific degradation or specific post-transcriptional gene silencing (PTGS) of messenger RNA (mRNA) transcribed from that targeted gene[72], thereby inhibiting expression of the target gene. In one embodiment, the RNA is double stranded RNA (dsRNA). This process has been described in plants, invertebrates, and mammalian cells. In nature, RNAi is initiated by the dsRNA-specific endonuclease Dicer, which promotes processive cleavage of long dsRNA into double-stranded fragments termed siRNAs. siRNAs are incorporated into a protein complex (termed "RNA induced silencing complex," or "RISC") that recognizes and cleaves target mRNAs. RNAi can also be initiated by introducing nucleic acid molecules, e.g., synthetic siRNAs or RNA interfering agents, to inhibit or silence the expression of target genes.

In the invention disclosed herein, the effector sequence can encode an RNA interference molecule to silence one or more genes in a target cell. Alternatively, the inhibitory nucleic acid construct can encode for an RNA interference molecule to silence the sensor construct transcript. In some cases both the effector sequence and inhibitory nucleic acid construct can encode RNA interference molecules, for example, siRNA, miRNA, shRNA or other double stranded RNA molecule.

Short interfering RNA (siRNA) is defined as an RNA agent which functions to inhibit expression of a target gene, e.g., by RNAi. An siRNA may be chemically synthesized, may be produced by in vitro transcription, or may be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, 22, or 23 nucleotides in length, and may contain a 3' and/or 5' overhang on each strand having a length of about 0, 1, 2, 3, 4, or 5 nucleotides. The length of the overhang is independent between the two strands, i.e., the length of the overhang on one strand is not dependent on the length of the overhang on the second strand. Preferably the siRNA is capable of promoting RNA interference through degradation or specific post-transcriptional gene silencing (PTGS) of the target messenger RNA (mRNA).

siRNAs also include small hairpin (also called stem loop) RNAs (shRNAs). In one embodiment, these shRNAs are composed of a short (e.g., about 19 to about 25 nucleotide) antisense strand, followed by a nucleotide loop of about 5 to about 9 nucleotides, and the analogous sense strand. Alternatively, the sense strand may precede the nucleotide loop structure and the antisense strand may follow.

The target gene or sequence of the RNA interfering agent may be a cellular gene or genomic sequence, e.g., those described herein as target genes. An siRNA may be substantially homologous to the target gene or genomic sequence, or a fragment thereof. As used in this context, the term "homologous" is defined as being substantially identical, sufficiently complementary, or similar to the target mRNA, or a fragment thereof, to effect RNA interference of the target. In addition to native RNA molecules, RNA suitable for inhibiting or interfering with the expression of a target sequence include RNA derivatives and analogs. Preferably, the siRNA is identical to its target.

The siRNA preferably targets only one sequence. Each of the RNA interfering agents, such as siRNAs, can be screened for potential off-target effects by, for example, expression profiling. Such methods are known to one skilled in the art and are described, for example, in Jackson et al. (2003)[73]. In addition to expression profiling, one may also screen the potential target sequences for similar sequences in the sequence databases to identify potential sequences which may have off-target effects. For example, according to Jackson et al.[73] 15, or perhaps as few as 11 contiguous nucleotides, of sequence identity are sufficient to direct silencing of non-targeted transcripts. Therefore, one may initially screen the proposed siRNAs to avoid potential off-target silencing using the sequence identity analysis by any known sequence comparison methods, such as BLAST.

siRNA sequences are chosen to maximize the uptake of the antisense (guide) strand of the siRNA into RISC and thereby maximize the ability of RISC to target human GGT mRNA for degradation. This can be accomplished by scanning for sequences that have the lowest free energy of binding at the 5'-terminus of the antisense strand. The lower free energy leads to an enhancement of the unwinding of the 5'-end of the antisense strand of the siRNA duplex, thereby ensuring that the antisense strand will be taken up by RISC and direct the sequence-specific cleavage of the target gene transcript.

siRNA molecules need not be limited to those molecules containing only RNA, but, for example, further encompasses chemically modified nucleotides and non-nucleotides, and also include molecules wherein a ribose sugar molecule is substituted for another sugar molecule or a molecule which performs a similar function. Moreover, a non-natural linkage between nucleotide residues can be used, such as a phosphorothioate linkage. The RNA strand can be derivatized with a reactive functional group of a reporter group, such as a fluorophore. Particularly useful derivatives are modified at a terminus or termini of an RNA strand, typically the 3' terminus of the sense strand. For example, the 2'-hydroxyl at the 3' terminus can be readily and selectively derivatized with a variety of groups.

Other useful RNA derivatives incorporate nucleotides having modified carbohydrate moieties, such as 2'O-alkylated residues or 2'-O-methyl ribosyl derivatives and 2'-O-fluoro ribosyl derivatives. The RNA bases may also be modified. Any modified base useful for inhibiting or interfering with the expression of a target sequence may be used. For example, halogenated bases, such as 5-bromouracil and 5-iodouracil can be incorporated. The bases may also be alkylated, for example, 7-methylguanosine can be incorporated in place of a guanosine residue. Non-natural bases that yield successful inhibition can also be incorporated.

The most preferred siRNA modifications include 2'-deoxy-2'-fluorouridine or locked nucleic acid (LAN) nucleotides and RNA duplexes containing either phosphodiester or varying numbers of phosphorothioate linkages. Such modifications are known to one skilled in the art and are described, for example, by Braasch et al., (2003)[74]. Most of the useful modifications to the siRNA molecules can be introduced using chemistries established for antisense oligonucleotide technology. Preferably, the modifications involve minimal 2'-O-methyl modification, preferably excluding such modification. Modifications also preferably exclude modifications of the free 5'-hydroxyl groups of the siRNA.

Synthetic siRNA molecules, including shRNA molecules, can be obtained using a number of techniques known to those of skill in the art. For example, the siRNA molecule can be chemically synthesized or recombinantly produced using methods known in the art, such as using appropriately protected ribonucleoside phosphoramidites and a conventional DNA/RNA synthesizer (see, e.g.,[75-79]). Alternatively, several commercial RNA synthesis suppliers are available including, but not limited to, Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA), and Cruachem (Glasgow, UK). As such, siRNA molecules are not overly difficult to synthesize and are readily provided in a quality suitable for RNAi. In addition, dsRNAs can be expressed as stem loop structures encoded by plasmid vectors, retroviruses and lentiviruses[80-87]. These vectors generally have a polIII promoter upstream of the dsRNA and can express sense and antisense RNA strands separately and/or as a hairpin structures. Within cells, Dicer processes the short hairpin RNA (shRNA) into effective siRNA.

The targeted region of the siRNA molecule of the present invention can be selected from a given target gene sequence. Nucleotide sequences may contain 5' or 3' UTRs and regions near the start codon. One method of designing a siRNA molecule of the present invention involves identifying the 23 nucleotide sequence motif AA(N19)TT (where N can be any nucleotide) and selecting hits with at least 25%, 30%, 35%, 40%, 45%, 50%, 55%, 60%, 65%, 70% or 75% G/C content. The "TT" portion of the sequence is optional. Alternatively, if no such sequence is found, the search may be extended using the motif NA(N21), where N can be any nucleotide. In this situation, the 3' end of the sense siRNA may be converted to TT to allow for the generation of a symmetric duplex with respect to the sequence composition of the sense and antisense 3' overhangs. The antisense siRNA molecule may then be synthesized as the complement to nucleotide positions 1 to 21 of the 23 nucleotide sequence motif. The use of symmetric 3' TT overhangs may be advantageous to ensure that the small interfering ribonucleoprotein particles (siRNPs) are formed with approximately equal ratios of sense and antisense target RNA-cleaving siRNPs[75,76]. Analysis of sequence databases, including but not limited to the NCBI, BLAST, Derwent and GenSeq as well as commercially available oligosynthesis companies such as Oligoengine®, may also be used to select siRNA sequences against EST libraries to ensure that only one gene is targeted.

Switches

The nucleic acid encoding a gene sensor can be further equipped with a switch as described previously by Gardner et al, 2000[47] (incorporated herein by reference), that allows for generation of a threshold-dependent output rather than a continuous set of output values. A switch may consist of a repressor, which inhibits the expression of the sensor construct until an agent is applied to permit expression. The incorporation of switches can tightly regulate the gene sensor to limit leakiness and unintended cell death, allowing for safer treatment modalities in a host. Further support is provided by Kobayashi, H. et al (2004) PNAS 101(22): 8414-8419, which is incorporated herein by reference[96].

The nucleic acid encoding the gene sensor is equipped at least with a promoter that is active in the target cell, however the choice of promoter can be tailored to target a specific cell population or intracellular condition (e.g., presence of an agent). For example, the gene sensor can be expressed highly in muscle tissue by utilizing the myosin heavy chain promoter on the gene sensor. Various other promoters are known by those skilled in the art.

Target Cell Types

The determination of target cell types is widely variable and can be altered to meet the specific user's needs. Indeed, the target cell type can range from various bacterial organisms to various eukaryotic cells. In one embodiment, bacterial cells that are associated with antibiotic resistance are utilized and include (but are not limited to) methicillin-resistant *Staphylococcus Aureus* (MRSA), vancomycin-resistant *Staphylococcus Aureus* (VSA), *Clostridium difficile*, *Streptococcus pneumoniae*, vancomycin-resistant *Enterococcus faecalis*, *Escherichia coli*, *Neisseria gonorrhoeae*, and *Pseudomonas aeruginosa*.

In another embodiment, cells involved are eukaryotic or mammalian in origin. In this context, the cell can be of any cell type including, but not limited to, epithelial, endothelial, neuronal, adipose, cardiac, skeletal muscle, fibroblast, immune cells, hepatic, splenic, lung, circulating blood cells, reproductive cells, gastrointestinal, renal, bone marrow, and pancreatic cells. The cell can be a cell line, a stem cell, or a primary cell isolated from any tissue including, but not limited to brain, liver, lung, gut, stomach, fat, muscle, testes, uterus, ovary, skin, endocrine organ and bone, etc.

Introduction of the Construct to a Cell

The nucleic acid molecule or molecules described herein can be introduced to the cell by any of a number of possible ways. In one embodiment, the cell is a bacterial cell, which allows the use of bacteriophage delivery systems to introduce the nucleic acid construct(s) to the cell. Bacteriophage therapy is becoming accepted in industrial and biotechnological settings. For example, the FDA recently approved the use of phage targeted at *Listeria monocytogenes* as a food additive[99]. Phage therapies have also been used successfully in Eastern Europe for over 60 years[100,101] and accordingly the methods of the present invention are applicable to human treatment. Even if not directly administered to humans or animals, bacteriophage provide a delivery vehicle for administering gene sensor and effector genes to bacteria, for example in a nosocomial setting or in a target population of bacteria outside of a human host (e.g., biofilm) (see [102-104], which are incorporated herein by reference)

The bacteriophage engineered to deliver sensor and/or inhibitor nucleic acid construct as described herein can be a lytic bacteriophage or lysogenic bacteriophage, or any bacteriophage that infects *E. coli*, *P. aeriginosa*, *S. aureaus*, *E. facalis* and the like and permit the addition of non-bacteriophage sequences. Such phages are well known to one skilled in the art, and include, but are not limited to, lambda phages, T7, T3, and T-even and T-even like phages, such as T2, and T4, and RB69; also phages such as Pf1, Pf4, Bacteroides fragilis phage B40-8 and coliphage MS-2 can be used. For example, lambda phage attacks *E. coli* by attaching itself to the outside of the bacterium and injecting its DNA into the bacterium. Once injected into the bacterial host, the phage uses *E. coli*'s genetic machinery to transcribe its genes. Any of the known phage vector systems can be engineered to express the gene sensor system described herein. Similarly, where a target species is infected by another bacteriophage, such bacteriophage can be adapted to use as a vector for the introduction of sensor and inhibitor constructs as described herein.

Some phages have been engineered to be more efficient cloning vectors or naturally lack a gene important in infecting all bacteria, such as male and female bacteria. These phages would also be suitable for developing the engineered phages of the present invention. Engineered bacteriophage are described in, for example, U.S. application Ser. Nos. 5,258,499 and 6,573,101, which are incorporated herein by reference in their entirety[90,91]. These bacteriophage were particularly suited to the attack of biofilms, e.g., including biofilms present in human organs, such as colon or lungs.

In another embodiment, the nucleic acid construct is introduced to the cell with a liposome molecule. Liposomes are the first nanotechnology to find use in a clinical setting. Liposomes are nano sized (50 nm-100 nm) artificial vesicles that are important new materials in the area of biotechnology, especially drug and nucleic acid delivery. Phospholipid liposomes have been used in the encapsulation of pharmaceuticals or supplements for delivery. The liposomic structure provides drugs a shield from external derogatory factors and can deliver the encapsulated pharmaceutical to cells via endocytosis. Recent advances in nanotechnology and molecular biology have enabled the creation of smart liposomes which can target specific cells/organs and which have programmed release of contents (nucleic acids, drugs etc) based on external or internal cues, e.g., pH, temperature or the presence of a complementary enzyme, among others. Use of liposome technology in terms of the method described herein relates to the encapsulation, protection from degradation and delivery of the nucleic acid construct or constructs to cells. Liposomes can be engineered such that the molecules are specifically targeted to a particular cell type by recognition of a receptor on the external surface of the cell (as previously disclosed, for example, in U.S. Pat. Nos. 5,258,499 and 6,573,101, which are incorporated herein by reference[92,93]). Liposomal delivery mechanisms comprising the nucleic acid constructs and variants described herein allow a wide variety of selectivity to treat specific disease states by selectively targeting liposomes to cells based on the surface expression of cellular receptors. For example, liposomes can be targeted to cancerous cells that express tumor antigens on the plasma membrane, thereby mediating the delivery of a gene sensor system as described herein to cells involved in tumor progression. Of course, part of the strength of the methods described herein is related to the restriction of effector gene expression to cells expressing a target gene. Thus, while liposomes or other delivery approaches can be tailored to target specific cells, even if such delivery is not 100% restricted to those cells, it is anticipated that the effector gene expression will be substantially limited to those cells expressed in the target gene.

In another embodiment, the nucleic acid molecule is introduced to bacterial cells in culture by bacterial transformation methods such as calcium chloride mediated transformation or other treatment rendering cells competent to take up exogenous nucleic acids. In another embodiment, the nucleic acid molecule is introduced to mammalian cells by the use of a viral delivery system (e.g., adenovirus, lentivirus). Both adenoviral and lentiviral vectors are capable of infecting dividing and non-dividing mammalian cells. Adenoviral vectors are often employed by those skilled in the art to produce a transient, high expression of a nucleic acid construct in question. Adenoviruses containing a nucleic acid construct are recognized by coxsackie receptors on the surface of mammalian cells, and subsequently enter the cell via endocytosis. The nucleic acid construct of adenoviral vectors is retained episomally, which does not permit cells to pass the nucleic acid construct information to daughter cells by genetic means. Alternatively, nucleic acid constructs delivered by a lentiviral system are incorporated into the host genome and thus are often employed for longer term expression, although at a lower expression level than that observed with adenoviral vectors.

In another embodiment, the nucleic acid molecule is introduced to cells in a human host in a conjugated form. The nucleic acid molecule can be conjugated, for example, to a cholesterol molecule, which may allow incorporation of the nucleic acid molecule into a circulating lipoprotein that would result in reduced clearance rates of the introduced construct. Alternatively, the nucleic acid molecule can be conjugated to an aptamer molecule (e.g., an oligonucleotide or polypeptide sequence), which can be targeted to a specific population of cells by altering the aptamer sequence to allow recognition by certain cell types. Similarly, the nucleic acid molecule can be conjugated to an antibody, which also allows cell specific recognition and uptake of the nucleic acid molecule. Additionally, the nucleic acid molecule can be conjugated to a cationic polypeptide and polymer mix to form stable nanoparticles, which can be incorporated with polyethylene glycol (PEG) to prevent aggregation of the particles.

In another embodiment, the nucleic acid molecule is introduced to localized tissues in vivo by direct localized injection with or without electroporation. The nucleic acid can be injected in e.g., an intra-ocular, intracerebroventricular, intrathecal, or intraparenchymal manner. In another embodiment, the nucleic acid is locally introduced to the airways by inhalation, intranasal or orotracheal administration. Alternatively, the nucleic acid molecule is delivered by a liposome designed to deliver the gene sensor to the target tissue by injection into the systemic circulation. Dosages of construct delivery agents will necessarily vary with respect to the target cell and the organism containing the target cell. Thus, for example, where the target cell is compared by a higher eukaryote, e.g., a mammal, the dose could be adapted in that animal, or will act as the specific delivery agent and delivery avenue. Thus, localized injection, for example, would require a lower dose than, for example, systemic injection. Similarly, a targeted delivery approach would be expected to require a lower dose than a non-targeted delivery approach. Where, for example, the constructs are to be introduced to a bacterial cell, the dosage will preferably be adjusted in relation to the size of the target cell population, i.e, higher doses, such as higher multiplicity of infection (MOI) where bacteriophage are concerned, can be used when the bacterial cell population is larger, relative to another population. MOI can be adjusted by the skilled artisan as necessary to achieve the desired level of delivery.

In another embodiment, bacteria can be transformed with the nucleic acid encoding the gene sensor such that the components are expressed in the bacterial cells. The transformed bacteria can then be used to deliver the components into mammalian cells as has been previously described by Xiang et el[68].

Dosing and Efficacy

Those skilled in the art of administration and dose regimes can determine the appropriate dose required for disease management using the gene sensor technology described herein. The efficacy of the gene sensor technology can be determined by a reduction in symptoms, for example skin lesions from infection with *Staphylococcus Aureus*. Alternatively, the efficacy can be measured by a reduction in the severity of disease as determined by one skilled in the art of diagnosis based on a measurable disease severity grading scale such as, for example the NYHA Classes of Heart failure. In this example, there are four stages of heart failure graded from mild to severe, based on symptoms such as e.g., the ability to carry on physical activity, shortness of breath, and palpitations. Efficacy can be measured in this example by the movement of a patient from e.g., a Class IV (severe) heart failure profile to a Class III, Class II, or Class I heart failure profile. Similar grading scales exist, for example, for heart disease, diabetic retinopathy, systemic sclerosis, Clostridium difficile—Associated Disease, Lipodystrophy Severity Grading Scale, HIV Outpatient Study scale, among others, which can be used to determine a patients' progress in response to treatment. Any positive change resulting in e.g., lessening of severity of disease measured using the appropriate scale, represents adequate treatment using the gene sensor described herein.

A treatment is considered "effective treatment," as the term is used herein, if any one or all of the signs or symptoms of e.g., a biofilm associated disease or cancer are altered in a beneficial manner or other clinically accepted symptoms or markers of disease are improved, or even ameliorated, e.g., by at least 10% following treatment involving a gene sensor as described herein. Efficacy can also be measured by a failure of an individual to worsen as assessed by hospitalization or need for medical interventions (i.e., progression of the disease is halted or at least slowed). Methods of measuring these indicators are known to those of skill in the art and/or described herein. Treatment includes any treatment of a disease in an individual or an animal (some non-limiting examples include a human, or a mammal) and includes: (1) inhibiting the disease, e.g., arresting, or slowing the pathogenic growth of e.g., a bacterium, a virus, or a fungus; or (2) relieving the disease, e.g., causing regression of symptoms, reducing the level of infection; and (3) preventing or reducing the likelihood of the development of infection e.g., in an immunocompromised individual.

Determining Reference Level and Measuring Expression

In the methods of target gene detection described herein, the expression of the effector gene sequence is preferably monitored by comparing the level of effector gene expression to a reference level.

To determine the reference level, the sensor and inhibitor construct(s) is/are delivered to a cell that does not express the target gene (referred to herein as a "control" or "reference" cell). Confirmation that a cell lacks target gene expression is performed, for example, at the mRNA level utilizing quantitative Real-Time PCR with target gene specific primers or Northern blot analysis with target gene specific probes. Alternatively, when the target gene is, e.g., a resistance gene, the lack of the target gene in a reference population or cell can be confirmed by treatment of cells with the agent to which the target gene confirms resistance. Once a reference cell has been established to lack the target gene, the sensor and inhibitor nucleic acid construct(s) is/are introduced to the cells by a delivery mechanism as known in the art of as described herein (e.g., bacteriophage, liposomes, viral carriers). It is preferred that the effector gene expression is determined by fluorescence of a reporter molecule (e.g., FACS), however effector gene expression can also be determined by PCR, Northern blot analysis or Western blot analysis. Where the effector is a reporter, the normal avenue of reporter detection is followed. The level of effector expression in cells lacking target gene expression denotes the reference level of the system.

To measure or titrate the expression of an effector molecule, the nucleic acid construct is delivered to a population of cells known to express the target gene of interest. Analysis of reporter gene expression can be determined, for example, by sorting cells using a fluorescence assisted cell sorter (FACS) machine according to the level of fluorescence detected when the reporter is a fluorescent molecule. The intensity of fluorescence in cells that actively express the target gene is normalized to the intensity of fluorescence in cells that do not actively express the target gene. The amounts of inhibitory nucleic acid construct or expression, or the amounts of sensor construct or expression, can be fine tuned with control or reference populations known to express or not express the target gene, as the case may be. Amounts of inhibitory nucleic acid can be adjusted, for example, by increasing or decreasing the amount of construct in produced strength of promoter from which it is expressed. Similar adjustments can be applied to the sensor construct.

Mediating Inhibition

In order to determine the portion of the target sequence that is sufficient to mediate inhibition by an inhibitory nucleic acid sequence as described herein, the sensor construct and the inhibitory nucleic acid construct can first be encoded on two separate nucleic acid molecules (e.g., vectors). In cells previously determined to express the target gene, the sensor construct is preferably expressed at a maximal level of reporter expression, such that a further increase in sensor construct delivery does not result in an increase in reporter expression. The nucleic acid molecule encoding the inhibitory nucleic acid molecule is then delivered in varying amounts to titrate the amount of expression. Any resulting changes in reporter expression as a result of altering the dose of inhibitory nucleic acid is analyzed and the inhibition level assessed. If there is no inhibition or very little inhibition of reporter fluorescence with a reasonable dose of inhibitory nucleic acid, then the portion of the target sequence coupled to the effector is not sufficient to mediate inhibition by binding to the inhibitory nucleic acid sequences. The length of the target gene portion of the sensor construct can be altered to modify the strength of binding to the inhibitory nucleic acid sequence. Generally, nucleic acid sequences bind in a strong manner when the sequences have a low degree of mis-match, and/or contain a high G-C content. These characteristics can be considered in the design of the sensor construct.

It is also contemplated herein that the threshold of the sensor is adjusted by modifying the antisense RNA sensor to bind more or less tightly to the target or the effector. The amount of acceptable selective sensing will depend on the application and can be determined by one of skill in the art.

Gene Sensor Detection Kit

Disclosed herein is a gene sensor detection kit comprising the gene sensor described herein and packaging materials therefor. The kit will contain nucleic acids encoding a sensor construct and an inhibitory nucleic acid vector, reagents, and instructions for proper use. As in other aspects described herein, the sensor construct and inhibitory nucleic acid construct can be present on separate vectors, or, preferably, on the same vector.

In one aspect, the kits described herein contain one or more control or reference cells, e.g., a positive control that expresses a target gene, and/or a negative control that does not express the target gene. The kits can further comprise reagents necessary for the delivery of the construct(s) to cells, e.g., liposomes or other delivery reagents, as well as, for example, antibiotics or other drugs suitable to test the system in a given setting.

In one aspect, a kit is adapted to be used on in vitro samples, e.g., taken from a patient suspected of harboring a resistant cell. Samples can comprise, for example, blood, serum, urine, sputum, a tissue sample, or any other biological sample derived from a subject suspected to harbor a target organism.

The methods and compositions described herein lend themselves to a number of different applications, of varying scope. Further aspects of the methods, compositions and kits described herein include at least the following.

FURTHER EMBODIMENTS

It can be advantageous to use the gene sensor approaches described herein to detect not just individual genes, such as resistance genes, but also to detect broader genera of targets. For example, in one aspect, the target gene is characteristic of a particular group of organisms, e.g., bacteria, fungi or viruses. In such aspects, a panel of gene sensor targets can be employed to quickly determine whether a sample contains, for example, a bacterium, a virus, or a fungus. This approach can provide reagents to narrow the possibilities for an agent of disease or type of contamination present. Possibilities for the detection of such genera include, for example, detection of bacterial ribosomal RNA or other gene targets characteristic of bacteria. Viruses can be detected by targeting, for example, viral polymerase, viral integrase, viral thymidine kinase, or other genes characteristic of viruses. Fungi can be targeted in a similar manner using a gene target or targets on a panel that are characteristic of fungi. This approach can be modified to include, rather than a single target that is characteristic of a given genera, e.g., bacteria in general, a panel of targets that would be diagnostic for any of a number of different members of the genus, e.g., gram negative bacteria, gram positive bacteria, or particular groups of bacteria, e.g., cocci, mycobacteria, spirochetes, etc. If desired, any such panel can be further segmented, or sub-panels provided, e.g., to provide markers specific for particular subgroups, up to and including specific species, e.g., *Staphylococcus aureus*, or even methicillin-resistant *Staphylococcus aureus*, as but a few examples. In this manner, the methods described herein can be used to prepare panels of varying degrees of specificity for different uses in a clinical, veterinary, agricultural or industrial setting. Kits containing such panels and reagents necessary to use them are specifically contemplated herein.

A multiplex format can also be used for the methods described herein. That is, gene sensor circuit reagents (including, at a minimum, a gene sensor construct and an inhibitory nucleic acid construct specific for the target of the sensor) for a plurality (i.e., at least two, at least three, at least four, at least five or more) of targets can be included in kits for the introduction to a desired cell type. In this aspect, each effector for each different target provides signal or read-out (i.e., reporter activity) that is distinguishable from that of each of the other effectors. As with other aspects described herein, the constructs making up the individual sensor circuits can be integrated into one vector or into separate vectors designed to function in the same cell type. In this manner, the circuits described herein can be used to determine which of a plurality of targets is present in a given population of cells. In this aspect, as in others described herein, effectors can include, as but a few examples, fluorescent proteins with distinguishable emission spectra, or enzymes that generate different colorimetric read-outs with appropriate substrates.

Finally, the embodiments described herein generally focus on a situation in which effector expression is maintained in an "off" position unless a target gene is expressed. However, circuits in which effector expression is in the "on" position as a default in the absence of target gene expression, and becomes down-regulated when the target gene is expressed are specifically contemplated.

It is understood that the foregoing detailed description and the following examples are illustrative only and are not to be taken as limitations upon the scope of the invention. Various changes and modifications to the disclosed embodiments, which will be apparent to those skilled in the art, may be made without departing from the spirit and scope of the present invention. Further, All patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The present invention may be as defined in any one of the following numbered paragraphs:

1. A method of detecting a cell expressing a target gene comprising the steps of:
   a. introducing to the cell a nucleic acid construct encoding a portion of the target gene sequence, fused to an effector gene sequence, and a construct encoding an inhibitory nucleic acid sequence directed against at least the portion of the target gene sequence, wherein in the absence of the target gene, the inhibitory nucleic acid sequence suppresses effector gene expression; and
   b. monitoring expression of the effector gene sequence in the cell and comparing the level of effector gene expression to a reference level, wherein if expression of the effector gene is increased relative to the reference level, the target gene is detected in the cell.

2. The method of paragraph 1, wherein the target gene is a mutant gene.
3. The method of paragraph 1 or 2, wherein the nucleic acid construct encoding a portion of the target gene sequence, fused to a the effector gene sequence, and the construct encoding an inhibitory nucleic acid sequence are encoded on the same nucleic acid molecule.
4. The method of paragraph 1, 2, or 3, wherein the cell is a bacterial cell.
5. The method of paragraph 1, 2 or 3, wherein the cell is a eukaryotic cell.
6. The method of any one of paragraphs 1-4, wherein the target gene is a drug resistance or virulence gene.
7. The method of any one of paragraphs 1-6, wherein the target gene is a multi-drug resistance (MDR) transporter gene.
8. The method of any one of paragraphs 1-7, wherein the target gene is a viral gene.
9. The method of any one of paragraphs 1-8, wherein the target gene is an oncogene or tumor associated gene.
10. The method of any one of paragraphs 1-9, wherein the effector gene sequence encodes a reporter molecule.
11. The method of any one of paragraphs 1-10, wherein the reporter comprises a polypeptide selected from the group consisting of an enzyme, a fluorescent polypeptide, a luminescent polypeptide and an antigen.
12. An engineered gene sensor comprising a nucleic acid sequence encoding a portion of a target gene sequence fused to an effector gene sequence and further comprising a construct encoding an inhibitory nucleic acid sequence directed against at least the portion of the target gene sequence, wherein the presence of the target gene expression in a cell permits the effector gene expression to produce an effector polypeptide which mediates delivery of an agent or mediates cell killing.
13. The gene sensor of paragraph 12, wherein the nucleic acid construct encoding a portion of the target gene sequence, fused to a the effector gene sequence, and the construct encoding an inhibitory nucleic acid sequence are encoded on the same nucleic acid molecule.
14. The gene sensor of paragraph 12 or 13, wherein the nucleic acid molecule comprises a vector.
15. The gene sensor of paragraph 12, 13, or 14, wherein the target gene is a drug resistance or virulence gene.
16. The gene sensor of any one of paragraphs 12-15, wherein the target gene is a multi-drug resistance (MDR) transporter gene.
17. The gene sensor of any one of paragraphs 12-16, wherein the target gene is a viral gene.
18. The gene sensor of any one of paragraphs 12-17, wherein the target gene is an oncogene or tumor associated gene.
19. The gene sensor of any one of paragraphs 12-18, wherein the effector gene sequence encodes a reporter molecule.
20. The gene sensor of any one of paragraphs 12-19, wherein the reporter comprises a polypeptide selected from the group consisting of an enzyme, a fluorescent polypeptide, a luminescent polypeptide and an antigen.
21. A method of selectively killing a cell expressing a target gene, the method comprising the steps of introducing to the cell a nucleic acid construct encoding a portion of the target gene sequence, fused to an effector gene sequence, and a construct encoding an inhibitory nucleic acid sequence directed against at least the portion of the target gene sequence,
   wherein in the absence of target gene expression, the inhibitory nucleic acid sequence suppresses expression of the effector gene, and wherein the presence of target gene expression in the cell permits effector gene expression to produce an effector polypeptide, and wherein expression of the effector polypeptide mediates cell killing.

22. The method of paragraph 21, wherein the cell is a bacterial cell.

23. The method of paragraph 21 or 22, wherein the cell is a eukaryotic/mammalian cell.

24. The method of paragraph 21, 22, or 23, wherein the target gene is a drug resistance or virulence gene.

25. The method of any one of paragraphs 21-24, wherein the target gene is a mutant gene.

26. The method of any one of paragraphs 21-25, wherein the target gene is a MDR transporter gene.

27. The method of any one of paragraphs 21-26, wherein the target gene is an oncogene.

28. The method of any one of paragraphs 21-27, wherein the target gene is a viral gene.

29. The method of any one of paragraphs 21-28, wherein the effector gene sequence encodes a polypeptide that mediates cell killing.

30. The method of any one of paragraphs 21-29, wherein the effector gene sequence encodes an RNA interference molecule.

31. The method of any one of paragraphs 21-30, wherein the effector is an apoptotic gene.

32. The method of any one of paragraphs 21-31, wherein the effector inhibits angiogenic pathways.

33. A system for detecting a target gene, the system comprising:
   a. a nucleic acid construct encoding a portion of the target gene sequence, fused to an effector gene sequence; and
   b. a construct encoding an inhibitory nucleic acid sequence that inhibits the target gene expression, wherein the nucleic acid constructs of (a) and (b) are comprised by the same nucleic acid molecule.

34. The system of paragraph 33, wherein the nucleic acid molecule comprises a vector.

35. The system of paragraph 33 or 34, wherein the vector is selected from the group consisting of: a plasmid vector, a viral vector and a bacteriophage vector.

36. The system of paragraph 33, 34 or 35, wherein the effector gene sequence encodes a reporter.

37. The system of paragraph 36, wherein the reporter comprises a polypeptide selected from the group consisting of an enzyme, a fluorescent polypeptide, a luminescent polypeptide and an antigen.

38. The system of any one of paragraphs 33-37, wherein the effector gene sequence encodes a polypeptide that mediates cell killing.

39. The system of any one of paragraphs 33-38, wherein the effector gene sequence encodes an RNA interference molecule.

40. The system of any one of paragraphs 33-39, wherein the target gene sequence is comprised by a drug resistance gene or a virulence gene.

41. The system of any one of paragraphs 33-40, wherein the target gene is an MDR transporter gene.

42. The system of any one of paragraphs 33-41, wherein the target gene sequence is comprised by a viral gene.

43. The system of any one of paragraphs 33-42, wherein the target gene sequence is comprised by a target oncogene or tumor associated gene.

44. The system of any one of paragraphs 33-43, wherein the effector is an apoptotic gene.

45. The system of any one of paragraphs 33-44, wherein the effector inhibits angiogenic pathways.

46. A kit for detecting a target gene, the system comprising:
   a. a nucleic acid construct encoding a portion of the target gene sequence, fused to an effector gene sequence;
   b. a construct encoding an inhibitory nucleic acid sequence that inhibits the target gene expression, wherein the nucleic acid constructs of (a) and (b) are comprised by the same nucleic acid molecule; and
   c. packaging materials therefore.

47. The kit of paragraph 46, wherein the nucleic acid construct encoding a portion of the target gene sequence, fused to a the effector gene sequence, and the construct encoding an inhibitory nucleic acid sequence are encoded on the same nucleic acid molecule.

48. The kit of paragraph 46 or 47, wherein the nucleic acid molecule comprises a vector.

49. The kit of paragraph 46, 47, or 48, wherein the target gene is a drug resistance or virulence gene.

50. The kit of any one of paragraphs 46-49, wherein the target gene is a multi-drug resistance (MDR) transporter gene.

51. The kit of any one of paragraphs 46-49, wherein the target gene is a viral gene.

52. The kit of any one of paragraphs 46-51, wherein the target gene is an oncogene or tumor associated gene.

53. The kit of any one of paragraphs 46-52, wherein the effector gene sequence encodes a reporter molecule.

54. The kit of any one of paragraphs 46-53, wherein the reporter comprises a polypeptide selected from the group consisting of an enzyme, a fluorescent polypeptide, a luminescent polypeptide and an antigen.

55. Use of a nucleic acid construct encoding a portion of a target gene sequence, fused to an effector gene sequence, and a construct encoding an inhibitory nucleic acid sequence directed against at least a portion of the target gene sequence for selectively killing a cell, the use comprising introducing the nucleic acid sequence to a cell.
   wherein in the absence of the target gene sequence, the inhibitory nucleic acid sequence suppresses effector gene expression, and
   wherein the presence of target gene expression in the cell permits effector gene expression to produce an effector polypeptide, and wherein expression of the effector polypeptide mediates cell killing.

56. Use of an engineered sensor comprising a nucleic acid sequence encoding a portion of a target gene sequence fused to an effector gene sequence and further comprising a construct encoding an inhibitory nucleic acid sequence directed against at least the portion of the target gene sequence for selectively killing a cell, the use comprising administering the engineered sensor to a cell,
   wherein the presence of the target gene expression in the cell permits the effector gene expression to produce an effector polypeptide which mediates delivery of an agent or mediates cell killing.

EXAMPLES

Example 1

A Bacterial Gene Sensor Circuit

As a first demonstration of the gene sensor circuit, described herein, an inhibitory nucleic acid construct was designed to express an antisense RNA target; the antisense resistance gene CAT. This was coupled with a sensor-effector construct with a portion of the CAT gene fused to GFP (odi) sequences. The read-out is GFP fluorescence.

Figure 4:
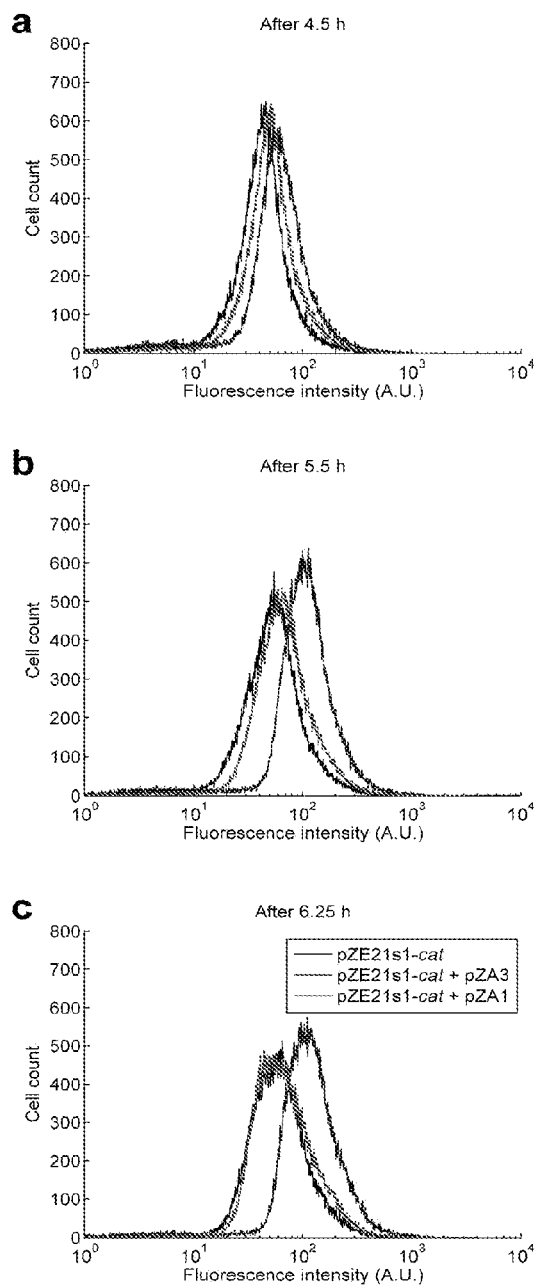
FIG. 4. A graph depicting the increase in expression of a reporter molecule compared to reference levels as indicated by the increase in fluorescence intensity in cells expressing the target gene after (a) 4.5 h, (b) 5.5 h and (c) 6.5 h of cell growth.

In one example, the paired-termini (PT7) design described by Nakashima et al, 2006[46] is extended to produce an antisense RNA similar to that shown in FIG. 1. The PT7 construct produces an antisense RNA with longer half-lives in vivo, allowing for greater antisense effect[46]. Starting with the PT7 construct shown in FIG. 1, the NcoI and XhoI restriction enzyme sites were replaced by HindIII and NheI sites, respectively. In this example, the target gene encodes for chloramphenicol resistance and is denoted as cat. This target gene represents a very well-characterized and important gene in *E. coli* encoding chloramphenicol resistance [94]. Using the paired-termini (PT) asRNA system[46], an antisense RNA was designed to target cat mRNA primarily in the 5'-untranslated region, the ribosome binding site (RBS) region, and the 5' end of the coding region (from the cat transcriptional start site to base pair 300 in the cat gene)[46]. DNA encoding antisense RNA to the antibiotic resistance gene target chloramphenicol acetyltransferase (cat, conferring chloramphenicol resistance ($Cm^R$)) was cloned in between HindIII and NheI sites near the top of the stem of the PT7 construct. The resulting PT7-cat-asRNA construct produces an antisense RNA that can bind to cat RNA and repress cat expression. The PT7-cat-asRNA was cloned under the inducible control of anhydrotetracycline (aTc) by using pZE21Y12α12GFP[95,105], taking care to remove the cis-repressive sequence and GFP. In order to design a plasmid that can detect the presence of target cat mRNA, the cat gene was fused with the gfp gene to produce a construct (cat-gfp) that is inhibited by PT7-cat-asRNA and thus produces low levels of GFP normally. A portion of cat DNA that encodes the 5'-untranslated region, the RBS, and the 5' end of the coding region was fused to gfp at a NotI restriction site. In this design, the cat-gfp fusion acts as the effector component (here, the effector is a reporter) while the PT7-cat-asRNA acts as the sensor component as depicted in FIG. 2. The cat-gfp fusion was then placed under the control of $P_{BAD}$ in the same vector as the sensor. The resulting sensor-reporter plasmid (pZE21s1-cat) was cloned into *E. coli* DH5αPro cells by itself or with a plasmid that either carried cat (pZA3) or bla (pZA1). pZA3 and pZA1 were both constructed from plasmids described by Lutz et al, 1997[95] with the synthetic promoters and genes removed by deleting all DNA between the XhoI and XmaI restriction sites. The pZE21s1-cat plasmid was introduced into *E. coli* DH5αPro cells alone[95,105], with a plasmid containing bla (pZA1), or with a plasmid containing cat (pZA3). GFP output in the presence of cat was approximately twice the output obtained in the presence of bla or without any plasmid at all as depicted in FIG. 4. Thus, pZE21s1-cat is able to detect the presence of a specific mRNA species encoding an antibiotic-resistance gene in vivo.

Example 2

Figure 5:
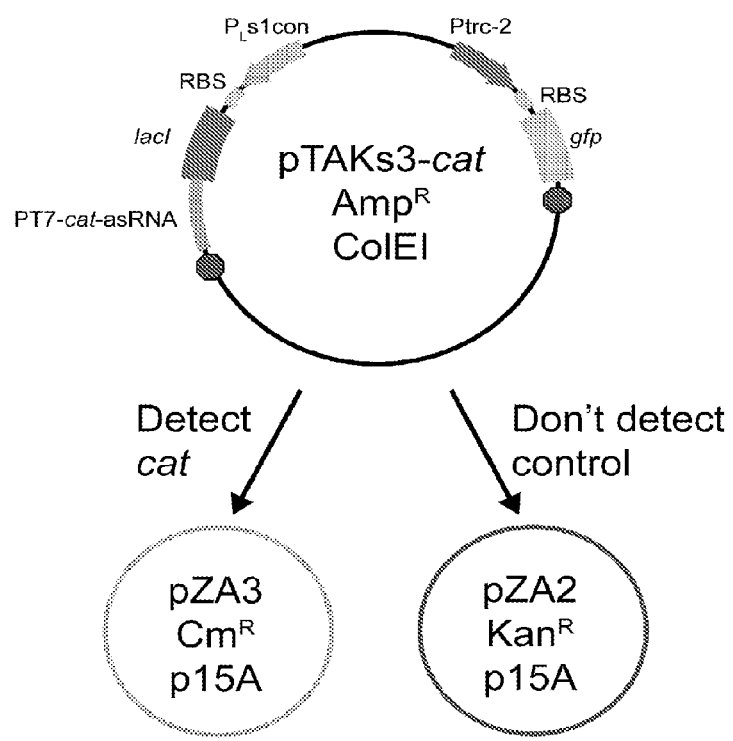
FIG. 5. A schematic depiction of a gene sensor molecule design that detects a target gene and effects the degradation of a repressor molecule, which in turn permits effector gene expression. (For further support see [47] incorporated from reference quoted herein)
Figure 7:
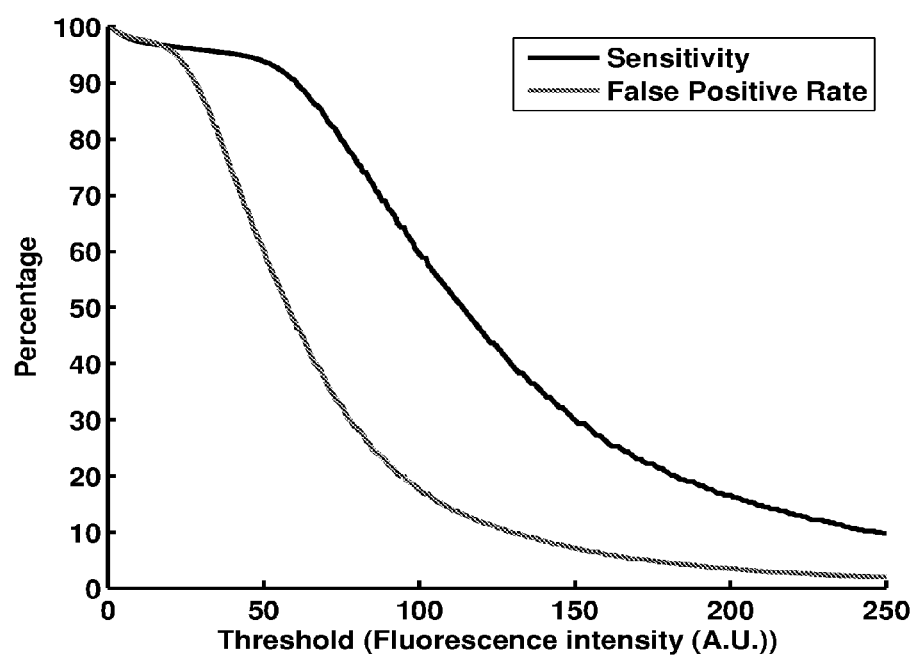
FIG. 7. A model for estimating selective sensing of a target gene.

In a second example, an RNA sensor design utilizes the pTAK series of plasmids described by Gardner et al, 2000[47]. Instead of cloning the antisense RNA for the target RNA into the upstream region of lacI, the PT7-cat-asRNA construct is placed downstream of the lacI gene to create pTAKs3-cat as depicted in FIG. 6. This design is utilized for target genes where the primary mode of the PT7 construct's antisense RNA action is through RNA degradation, as this system relies on lacI-PT7-cat-asRNA binding to cat mRNA to trigger degradation of the lacI-PT7-cat-asRNA RNA[46]. Reduction of the levels of the Lac repressor increase GFP output. The RNA sensor design shown in FIG. 5 is realized by cloning PT7-asRNA fragments into the AscI site in pTAK132 from Gardner et al, 2000[47]. The cI857 gene in pTAK132 is removed by restriction digest in order to obtain a continuous output behavior rather than discontinuous switch behaviour. This permits the effector molecule to be in two main states: on and off. The sensor-reporter plasmid (pTAKs3-cat) can be co-transformed with cat- or kan-containing plasmids (pZA3 or pZA2, respectively) for testing.

Example 3

The following example demonstrates how to determine the sensitivity and false positive rate of the gene sensor described herein. Generally, a higher false positive rate is preferred, i.e., greater sensitivity, at the potential expense of some false positives, as opposed to a higher false negative rate, in which positive cells are not detected.

DEFINITIONS

True Positive (TP)—cell has target gene and is sensed
False Negative (FN)—cell has target gene but is not sensed
True Negative (TN)—cell doesn't have target gene and is not sensed
False Positive (FP)—cell doesn't have target gene but is sensed Using standard statistical terms, let us define selective sensing as a low false-positive rate (meaning that a low number of cells that do not have the target are sensed or killed=FP/(TN+FP))

Still want respectable sensitivity (meaning that a good number of cells that do have the target are actually sensed=TP/(TP+FN))

FIG. 6 shows the sensitivity and false-positive rate on the Y-axis versus different thresholds on the X-axis (thresholds of fluorescence intensity) for FIG. 4c in "Gene Sensor Description.doc" (t=6.25 hours)

False-positives calculated for pZE21s1-cat (i.e. the situation where there is no target gene in the cells)

REFERENCES

All references cited in the specification and listed below, are herein incorporated by reference in their entirety.
1. Walsh, C., *Nat Rev Microbiol* 1:65-70 (2003).
2. Shah, D. et al., *BMC Microbiol.* 6:53 (2006).
3. Wise, R., *J. Antimicrob. Chemother.* 54:306-310 (2004).
4. Hall-Stoodley, L., Costerton, J. W. & Stoodley, P., *Nat Rev Microbiol* 2:95-108 (2004).
5. Levin, B. R. & Bonten, M. J. M., *Proc Natl Acad Sci USA* 101:13101-13102 (2004).
6. Projan, S., *Nat. Biotechnol.* 22:167-168 (2004).
7. Schoolnik, G. K., Summers, W. C. & Watson, J. D., *Nat. Biotechnol.* 22:505-506; author reply 506-507 (2004).
8. Vandenesch, F. et al., *Emerg. Infect. Dis.* 9:978-984 (2003).
9. From the Centers for Disease Control and Prevention. 1997-1999. JAMA 282:1123-1125 (1999).
10. Hall, B. G., *Nat Rev Microbiol* 2:430-435 (2004).
11. Alekshun, M. N. & Levy, S. B., *Cell* 128:1037-1050 (2007).
12. Morens, D. M., Folkers, G. K. & Fauci, A. S., *Nature* 430:242-249 (2004).
13. Salyers, A. A., Gupta, A. & Wang, Y., *Trends Microbiol.* 12:412-416 (2004).
14. Chang, S. et al., *N. Engl. J. Med.* 348:1342-1347 (2003).
15. Beaber, J. W., Hochhut, B. & Waldor, M. K., *Nature* 427:72-74 (2004).
16. Ubeda, C. et al., *Mol. Microbiol.* 56:836-844 (2005).

17. Martinez, J. L. & Baquero, F., Antimicrob. *Agents Chemother.* 44:1771-1777 (2000).
18. Klevens, R A M. et al., *JAMA* 298:1763-1771 (2007).
19. Balaban, N. Q., Merrin, J., Chait, R., Kowalik, L. & Leibler, S., *Science* 305:1622-1625 (2004).
20. Lewis, K., *Nat Rev Microbiol* (2006).
21. Wiuff, C. et al., *Antimicrob. Agents Chemother.* 49:1483-1494 (2005).
22. Lewis, K., *Biochemistry (Mosc).* 70:267-274 (2005).
23. Korch, S. B. & Hill, T. M., *J. Bacteriol.* 188:3826-3836 (2006).
24. Vázquez-Laslop, N., Lee, H. & Neyfakh, A. A., *J. Bacteriol.* 188:3494-3497 (2006).
25. Avery, S. V., *Nat Rev Microbiol.* 4:577-587 (2006).
26. Wang, J. et al., *Nature* 441:358-361 (2006).
27. Bergstrom, C. T., Lo, M. & Lipsitch, M., *Proc Natl Acad Sci USA* 101:13285-13290 (2004).
28. Brown, E. M. & Nathwani, D., *J. Antimicrob. Chemother.* 55:6-9 (2005).
29. Soulsby, E. J., *BMJ* 331:1219-1220 (2005).
30. Soulsby, L., *J. Antimicrob. Chemother.* 60 Suppl 1, i77-i78 (2007).
31. Hagens, S. & Blasi, U., *Lett. Appl. Microbiol.* 37:318-323 (2003).
32. Hagens, S., Habel, A. v. A. U., von Gabain, A. & Blasi, U., *Antimicrob. Agents Chemother.* 48:3817-3822 (2004).
33. Westwater, C. et al., *Antimicrob. Agents Chemother.* 47:1301-1307 (2003).
34. Heitman, J., Fulford, W. & Model, P., *Gene* 85:193-197 (1989).
35. Brüssow, H., *Microbiology* 151:2133-2140 (2005).
36. Summers, W. C., *Annu. Rev. Microbiol.* 55:437-451 (2001).
37. Loose, C., Jensen, K., Rigoutsos, I. & Stephanopoulos, G., *Nature* 443:867-869 (2006).
38. Lu, T. K. & Collins, J. J., *Proc Natl Acad Sci USA,* 104:11197-11202 (2007).
39. Bonhoeffer, S., Lipsitch, M. & Levin, B. R., *Proc Natl Acad Sci USA* 94:12106-12111 (1997).
40. Chait, R., Craney, A. & Kishony, R., *Nature* 446:668-671 (2007).
41. Levy, S. B. & Marshall, B., *Nat. Med.* 10:S122-S129 (2004).
42. Hagens, S., Habel, A. & Bläsi, U., *Microb Drug Resist* 12:164-168 (2006).
43. Dwyer, D. J., Kohanski, M. A., Hayete, B. & Collins, J. J., *Mol Syst Biol* 3:91 (2007).
44. Kohanski, M. A., Dwyer, D. J., Hayete, B., Lawrence, C. A. & Collins, J. J., *Cell* 130:797-810 (2007).
45. Coburn, G. and Cullen, B., *J. of Virology* 76(18):9225 (2002).
46. Nakashima, N., Tamura, T., and Good, L., *Nucleic Acids Res* 34:e138 (2006).
47. Gardner, T S., Cantor, C R. And Collins, J J., *Nature* 403:339-342 (2000).
48. Higgins, C F., *Nature Reviews* 446:749-757 (2007).
49. Aminov, R I and Mackie, R I., *FEMS Microbiol Lett* 271:147-161 (2007).
50. Wright, G D., *Nature Reviews* 5:175-186 (2007).
51. Alekshun, M N., and Levy, S B., *Cell* 128:1037-1050 (2007).
52. Cegelski, L., Marshall, G R., Edridge, G R. And Hultgren S J., *Nature Reviews Microbiology,* 6:17-27 (2008).
53. Piddock L J V., *Clinical Microbiology Reviews* 19(2):382-402 (2006).
54. Ceccarelli, M., Danelon, C., Laio, A., and Parrinello, M., *Biophysical Journal* 87: 58-64 (2004).
55. Clatworthy, A E., Pierson, E. and Hung D T., *Nature Chemical Biology* 3(9):541-548(2007).
56. U.S. Pat. No. 6,635,476.
57. Croce, C M., *New England Journal of Medicine,* 358:502-511 (2008).
58. Williams, S A., and Greene, W C., *Cytokine* 39:63-74 (2007).
59. Kay M S., *TRENDS in Biotechnology* 21(10):420-423 (2003).
60. Steiner, I., Kennedy P G E., and Pachner, A R., *Lancet Neurology* 6:1015-1028 (2007).
61. Efstathiou S., and Preston C M., *Virus Research* 111:108-119 (2005).
62. Engelberg-Kulka, H., Amitai, A., Kolodkin-Gal, I., and Hazan, R., *PLoS Genetics* 2(10):e135 (2006).
63. Gerdes, K., Christensen, S K., and Lobner-Olesen, A., *Nature Reveiws* 3:371-382 (2005).
64. Youle, R J., and Strasser A., *Nature Reviews* 9:47-59 (2008).
65. Meier, P. and Vousden, K H., *Molecular Cell* 28:746-754 (2007).
66. Bartsevich, V V. And Juliano, R L., *Molecular Pharmacology* 58:1-10 (2000).
67. Fougerolles, A., et al, *Nature Reviews Drug Discovery* 6:443-453 (2007).
68. Xiang, S., Fruehauf, J., and Li, C J., *Nature Biotechnology* 24(6):697-702 (2006).
69. Westwater, C., Kasman, L M., Schofield, D A., Werner, P A., Dolan, J W., Schmidt, M G., and Norris, J S., *Antimicrobial Agents and Chemotherapy,* 47(4):1301-1307 (2003).
70. Hagens, S., Habel, A., von Ahsen, U., von Gabain, A., and Blasi, U., *Antimicrobial Agents and Chemotherapy,* 48(10):3817-3822 (2004).
71. Hagens, S., and Blasi, U., *Letters in Applied Microbiology,* 37:318-32 (2003).
72. Coburn, G. and Cullen, B., *J. of Virology,* 76(18):9225 (2002).
73. Jackson, A L., Bartz, S R., Schelter, J., Kobayashi, S V., Burchard, J., Mao, M., Li, B., Cavet, G., Linsley, P S., *Nature Biotechnology,* 21(6):635-637 (2003).
74. Braasch et al., *Biochemistry,* 42: 7967-7975 (2003).
75. Elbashir, S. M. et al., *Nature,* 411:494-498 (2001).
76. Elbashir, S. M., W. Lendeckel and T. Tuschl, *Genes & Development,* 15:188-200 (2001).
77. Harborth, J. et al., *J. Cell Science,* 114:4557-4565 (2001).
78. Masters, J. R. et al., *Proc. Natl. Acad. Sci., USA* 98:8012-8017 (2001).
79. Tuschl, T. et al., *Genes & Development,* 13:3191-3197 (1999).
80. Paddison, P. J. et al., *Genes Dev.,* 16:948-958 (2002).
81. McManus, M. T. et al., *RNA,* 8:842-850 (2002).
82. Paul, C. P. et al., *Nat. Biotechnol.,* 20:505-508 (2002).
83. Miyagishi, M. et al., *Nat. Biotechnol.,* 20:497-500 (2002).
84. Sui, G. et al., *Proc. Natl. Acad. Sci., USA* 99:5515-5520 (2002).
85. Brummelkamp, T. et al., *Cancer Cell* 2:243 (2002).
86. Lee, N. S., et al., *Nat. Biotechnol.* 20:500-505 (2002).
87. Yu, J. Y., et al., *Proc. Natl. Acad. Sci. USA* 99:6047-6052 (2002).
88. Zeng, Y., et al., *Mol. Cell* 9:1327-1333 (2002).
89. Rubinson, D. A., et al., *Nat. Genet.* 33:401-406; (2003).
90. Stewart, S. A., et al., *RNA* 9:493-501 (2003).
91. U.S. Pat. No. 5,258,499.

92. U.S. Pat. No. 6,573,101.
93. U.S. Pat. No. 5,258,499.
94. U.S. Pat. No. 6,573,101.
95. Potrykus et al, *Antimicrobial Agents and Chemotherapy*, 45:3610-3612 (2001).
96. Lutz, R and Bujard, H., *Nucleic Acids Research* 25:1203-1210 (1997).
97. Kobayashi, H., Kaern, M., Araki, M., Chung, K., Gardner, T S., Cantor, C R., and Collins J J., *PNAS* 101(22):8414-8419 (2004).
98. Kolter, R. et al, *Nature* 443:867-769 (2006).
99. Costerton, J W., et al, *Science* 284:1318-1322 (1999).
100. Shuren, J., et al, *U.S. FDA*, 71:47729-47732 (2006).
101. Curtin, J J., and Donlan, R M., *Antimicrob Agents Chemother* 50:1268-1275 (2006).
102. Merril, C R., et al, *Nat Rev Drug Discov* 2:489-497 (2003).
103. Doolittle, M M., et al, *Can J Microbiol* 41:12-18 (1995).
104. Doolittle, M M., et al, *J Ind Microbiol* 16:331-341 (1996).
105. Corbin, B D., et al, *Can J Microbiol* 47:680-684 (2001).
106. Issacs, F J., et al, *Nat Biotechnol* 22:841-847 (2004).

TABLE 1

```
CTCGAG
TCCCTATCAGTGATAGAGATTGACATCCCTATCAGTGATAGAGATACTGAGCACATCAGCAGGACGCACTGACC
GAATTC
AGGAGGAATT AACCATGCAG TGGTGGTGGT GGTGGTG
AAGCTT
TATAGGTACATTGAGCAACTGACTGAAATGCCTCAAAATGTTCTTTACGATGCCATTGGGATATATCAACGGTGG
TATATCCAGTGATTTTTTTCTCCATTTTAGCTTCCTTAGCTCCTGAAAATCTCGATAACTCAAAAAATACGCCCG
GTAGTGATC
GCTAGC
CACCACC ACCACCACCA CTGCATGGTT AATTCCTCCT
CCCGGG
GGATCC
CATGGT
ACGCGT
GGCATCAAATAAAACGAAAGGCTCAGTCGAAAGACTGGGCCTTTCGTTTT
ATCTGTTGTTTGTCGGTGAACGCTCTCCTGAGTAGGACAAATCCGCCGCCCTAGA
CCTAGG

CGTTCGGCTGCGGCGAGCGGTATCAGCTCACTCAAAGGCGGTAATACGGTTATCCAC
AGAATCAGGGGATAACGCAGGAAAGAACATGTGAGCAAAAGGCCAGCAAAAGGCCAGGAACC
GTAAAAAGGCCGCGTTGCTGGCGTTTTTCCATAGGCTCCGCCCCCCTGACGAGCATCACAAA
AATCGACGCTCAAGTCAGAGGTGGCGAAACCCGACAGGACTATAAAGATACCAGGCGTTTCC
CCCTGGAAGCTCCCTCGTGCGCTCTCCTGTTCCGACCCTGCCGCTTACCGGATACCTGTCCG
CCTTTCTCCCTTCGGGAAGCGTGGCGCTTTCTCAATGCTCACGCTGTAGGTATCTCAGTTCG
GTGTAGGTCGTTCGCTCCAAGCTGGGCTGTGTGCACGAACCCCCCGTTCAGCCCGACCGCTG
CGCCTTATCCGGTAACTATCGTCTTGAGTCCAACCCGGTAAGACACGACTTATCGCCACTGG
CAGCAGCCACTGGTAACAGGATTAGCAGAGCGAGGTATGTAGGCGGTGCTACAGAGTTCTTG
AAGTGGTGGCCTAACTACGGCTACACTAGAAGGACAGTATTTGGTATCTGCGCTCTGCTGAA
GCCAGTTACCTTCGGAAAAAGAGTTGGTAGCTCTTGATCCGGCAAACAAACCACCGCTGGTA
GCGGTGGTTTTTTTGTTTGCAAGCAGCAGATTACGCGCAGAAAAAAAGGATCTCAAGAAGAT
CCTTTGATCTTTTCTACGGGGTCTGACGCTCAGTGGAACGAAAACTCACGTTAAGGGATTTT
GGTCATG

ACTAGT
GCTTGGATTCTCACCAATAAAAAACGCCCGGCGGCAACCGAGCGTTCTGAAC
AAATCCAGATGGAGTTCTGAGGTCATTACTGGATCTATCAACAGGAGTCCAAGC
GAGCTC
TCGAACCCCAGAGTCCCGCTCAGAAGAACTCGTCAAGAAGGCGATAGAAGGCGATGCGCTGCGAATCGGGAGCGG
CGATACCGTAAAGCACGAGGAAGCGGTCAGCCCATTCGCCGCCAAGCTCTTCAGCAATATCACGGGTAGCCAACG
CTATGTCCTGATAGCGGTCCGCCACACCCAGCCGGCCACAGTCGATGAATCCAGAAAAGCGGCCATTTTCCACCA
TGATATTCGGCAAGCAGGCATCGCCATGGGTCACGACGAGATCCTCGCCGTCGGGCATGCGCGCCTTGAGCCTGG
CGAACAGTTCGGCTGGCGCGAGCCCCTGATGCTCTTCGTCCAGATCATCCTGATCGACAAGACCGGCTTCCATCC
GAGTACGTGCTCGCTCGATGCGATGTTTCGCTTGGTGGTCGAATGGGCAGGTAGCCGGATCAAGCGTATGCAGCC
GCCGCATTGCATCAGCCATGATGGATACTTTCTCGGCAGGAGCAAGGTGAGATGACAGGAGATCCTGCCCCGGCA
CTTCGCCCAATAGCAGCCAGTCCCTTCCCGCTTCAGTGACAACGTCGAGCACAGCTGCGCAAGGAACGCCCGTCG
TGGCCAGCCACGATAGCCGCGCTGCCTCGTCCTGCAGTTCATTCAGGGCACCGGACAGGTCGGTCTTGACAAAAA
GAACCGGGCGCCCCTGCGCTGACAGCCGGAACACGGCGGCATCAGAGCAGCCGATTGTCTGTTGTGCCCAGTCAT
AGCCGAATAGCCTCTCCACCCAAGCGGCCGGAGAACCTGCGTGCAATCCATCTTGTTCAATCATGCGAAACGATC
CTCATCCTGTCTCTTGATCAGATCTTGATCCCCTGCGCCATCAGATCCTTGGCGGCAAGAAAGCCATCCAGTTTA
CTTTGCAGGGCTTCCCAACCTTACCAGAGGGCGCCCCAGCTGGCAATTCC
GACGTC
TTT
GGGCCC
AAGGCCCAGTCTTTCGACTGAGCCTTTCGTTTTATTTGATGCCTGGCAGTTCCCTACTCTCGCATGGGGAGACCC
CACACTACCATCGGCGCTACGCGTTTCACTTCTGAGTTCGGCATGGGGTCAGGTGGGACCACCGCGCTACTGCC
GCCAGGCAAATTCTGTT
TCTAGA
TTATTTGTATAGTTCATCCATGCCATGTGTAATCCCAGCAGCTGTTACAAACTCAAGAAGGACCATGTGGTCTCT
CTTTTCGTTGGGATCTTTCGAAAGGGCAGATTGTGTGGACAGGTAATGGTTGTCTGGTAAAAGGACAGGGCCATC
GCCAATTGGAGTATTTTGTTGATAATGGTCTGCTAGTTGAACGCTTCCATCTTCAATGTTGTGTCTAATTTTGAA
GTTAACTTTGATTCCATTCTTTTGTTTGTCTGCCATGATGTATACATTGTGTGAGTTATAGTTGTATTCCAATTT
GTGTCCAAGAATGTTTCCATCTTCTTTAAAATCAATACCTTTTAACTCGATTCTATTAACAAGGGTATCACCTTC
AAACTTGACTTCAGCACGTGTCTTGTAGTTCCCGTCATCTTTGAAAAATATAGTTCTTTCCTGTACATAACCTTC
GGGCATGGCACTCTTGAAAAAGTCATGCTGTTTCATATGATCTGGGTATCTCGCAAAGCATTGAACACCATAACC
GAAAGTAGTGACAAGTGTTGGCCATGGAACAGGTAGTTTTCCAGTAGTGCAAATAAATTTAAGGGTAAGTTTTCC
```

TABLE 1 -continued

GTATGTTGCATCACCTTCACCCTCTCCACTGACAGAAAATTTGTGCCCATTAACATCACCATCTAATTCAACAAG
AATTGGGACAACTCCAGTGAAAAGTTCTTCTCCTTTACG
C GCGGCCGC

*cgccccgccctgccactcatcgcagtactgttgtaattcattaagcattctgccgacatggaagccatcacagac*
*ggcatgatgaacctgaatcgccagcggcatcagcaccttgtcgccttgcgtataatatttgcccatggtgaaaac*
*gggggcgaagaagttgtccatattggccacgtttaaatcaaaactggtgaaactcacccagggattggctgagac*
*gaaaaacatattctcaataaaccctttagggaaataggccaggttttcaccgtaacacgccacatcttgcgaata*
*tatgtgtagaaactgccggaaatcgtcgtggtattcactccagagcgatgaaaacgtttcagtttgctcatggaa*
*aacggtgtaacaagggtgaacactatcccatatcaccagctcaccgtctttcattgccatacggaattccggatg*
*agcattcatcaggcgggcaagaatgtgaataaaggccggataaaacttgtgcttatttttctttacggtctttaa*
*aaaggccgtaatatccagctgaacggtctggttataggtacattgagcaactgactgaaatgcctcaaaatgttc*
*tttacgatgccattgggatatatcaacggtggtatatccagtgatttttttctccatttttagcttccttagctcc*
*tgaaaatctcgataactcaaaaaatacgcccggtagtgatc*

GTCGAC
TATGGAGAAACAGTAGAGAGTTGCGATAAAAAGCGTCAGGTAGGATCCGCTAATCTTATGGA
TAAAAATGCTATGGCATAGCAAAGTGTGACGCCGTGCAAATAATCAATGTGGACTTTTCTGC
CGTGATTATAGACACTTTTGTTACGCGTTTTTGTCATGGCTTTGGTCCCGCTTTGTTACAGA
ATGCTTTTAATAAGCGGGGTTACCGGTTTGGTTAGCGAGAAGAGCCAGTAAAAGACGCAGTG
ACGGCAATGTCTGATGCAATATGGACAATTGGTTTCTT (SEQ ID NO: 10)

TABLE 2

| Signature Name | Example Species |
|---|---|
| ADHERENCE/COLONIZATION FACTORS | |
| *Rickettsia* 56 kDa type-specific antigen protein | *Rickettsia tsutsugamushi* |
| Adhesin B | *Streptococcus pneumoniae* |
| *Neisseria meningitidis* adhesin MafB | *Neisseria meningitidis* |
| Adhesin family | *Streptococcus pneumoniae* |
| *Escherichia coli* P pili tip fibrillum papE protein | *Escherichia coli* |
| *Escherichia coli* P pili tip fibrillum papF protein | *Escherichia coli* |
| *Porphyromonas gingivalis* fimbrillin protein | *Porphyromonas gingivalis* |
| *Escherichia coli* P pili regulatory PapB protein | *Escherichia coli* |
| Flagellin | *Salmonella* spp. |
| Flagellar biosynthetic protein FliP | *Salmonella* spp. |
| Flagellar protein FlgJ | *Salmonella* spp. |
| Flagellar assembly protein FliH | *Salmonella* spp. |
| Flagellar FliJ protein | *Salmonella* spp. |
| Flagellar hook-associated protein | *Salmonella* spp. |
| Flagellar hook-basal body complex protein FliE | *Salmonella* spp. |
| Flagellar hook-length control protein | *Salmonella* spp. |
| Flagellar L-ring protein | *Salmonella* spp. |
| Flagellar motor switch protein FliG | *Salmonella* spp. |
| Flagellar motor switch protein FliM | *Salmonella* spp. |
| Flagellar motor switch protein FliN | *Salmonella* spp. |
| Flagellar M-ring protein | *Salmonella* spp. |
| Flagellar P-ring protein | *Salmonella* spp. |
| Macrophage infectivity potentiator | *Legionella pneumophila* |
| Sodium-type flagellar protein MotY precursor | *Salmonella* spp. |
| *Yersinia* outer membrane adhesin | *Yersinia* spp. |
| Type IV prepilin cysteine protease (C20) family | *Escherichia coli* |
| *Lactobacillus* surface layer protein | *Lactobacillus brevis* |
| INVASINS | |
| Gallidermin | *Streptococcus mutans* |
| IgA-specific serine endopeptidase (S6) | *Haemophilus influenzae* |
| Microbial collagenase metalloprotease (M9) | *Clostridium perfringens* |
| Bacterial phospholipase A1 protein | *Escherichia coli* |
| Prokaryotic zinc-dependent phospholipase C | *Clostridium perfringens* |
| Streptothricin acetyltransferase | *Escherichia coli* |
| *Streptococcus* streptokinase protein | *Streptococcus* spp. |
| Thermolysin metalloprotease (M4) family | *Bacillus* spp. |
| Urea amidohydrolase (urease) protein | *Escherichia coli* |
| CELL SURFACE FACTORS | |
| 60 kDa inner membrane protein | *Escherichia coli* |
| *Yersinia*/*Haemophilus* virulence surface antigen | *Yersinia pestis* |
| Bacterial lipocalin | *Vibrio cholerae* |
| Nucleoside-specific channel-forming protein Tsx | *Escherichia coli* |
| *Chlamydia* cysteine-rich outer membrane protein 3 | *Chlamydia trachomatis* |
| *Chlamydia* cysteine-rich outer membrane protein 6 | *Chlamydia trachomatis* |
| *Chlamydia* major outer membrane protein | *Chlamydia trachomatis* |
| *E. coli*/*Salmonella*-type porin | *Escherichia coli* |
| *E. coli*/*Neisseria* porin superfamily | *Escherichia coli* |

TABLE 2-continued

| Signature Name | Example Species |
| --- | --- |
| Enterobacterial virulence outer membrane protein | *Escherichia coli* |
| Gram-positive coccus surface protein anchor | *Streptococcus pyogenes* |
| Ice nucleation protein | *Pseudomonas* spp. |
| Low calcium response V antigen | *Yersinia pestis* |
| LPP20 lipoprotein precursor | *Helicobacter pylori* |
| *Neisseria* sp. porin | *Neisseria* spp. |
| Nucleotide sugar epimerase | *Vibrio vulnificus* |
| OMPA domain | *Escherichia coli* |
| OMS28 porin | *Borrelia burgdoferi* |
| Outer membrane protein A | *Escherichia coli* |
| Outer surface protein | *Borrelia burgdoferi* |
| EXOTOXINS | |
| Aerolysin | *Aeromonas hydrophila* |
| Anthrax toxin LF subunit | *Bacillus anthracis* |
| *Salmonella/Shigella* invasin protein C | *Salmonella* spp. |
| *Salmonella/Shigella* invasin protein B | *Salmonella* spp. |
| Bacterial toxin | *Streptococcus pyogenes* |
| Staphylococcal bi-component toxin | *Staphylococcus aureus* |
| Clostridial binary toxin A | *Clostridium* spp. |
| Binary toxin B family | *Clostridium* spp. |
| Bontoxilysin | *Clostridium botulinum* |
| *Bordetella pertussis* toxin A subunit | *Bordetella pertussis* |
| *Bordetella pertussis* toxin B subunit | *Bordetella pertussis* |
| NodO calcium binding | *Escherichia coli* |
| Cytolethal distending toxin A | *Escherichia coli* |
| Cytolethal distending toxin B | *Escherichia coli* |
| Channel forming colicin | *Escherichia coli* |
| *Clostridium* enterotoxin | *Clostridium* spp. |
| Cloacin | *Escherichia coli* |
| Diphtheria toxin | *Corynebacterium dihtheriae* |
| Heat-labile enterotoxin A chain | *Escherichia coli* |
| Heat labile enterotoxin B chain | *Escherichia coli* |
| Fragilysin metallopeptidase (M10C) enterotoxin | *Bacteroides fragilis* |
| *Helicobacter* neutrophil-activating protein A family | *Helicobacter pylori* |
| Intimin | *Escherchia coli* |
| *Salmonella/Shigella* invasion protein E (InvE) | *Salmonella* spp. |
| *Mycoplasma* P48 major surface lipoprotein | *Mycoplasma fermentans* |
| Nisin | *Bacillus subtilis* |
| Omptin serine protease | *Escherchia coli* |
| Pertactin | *Bordetella pertussis* |
| Pertactin virulence factor family | *Bordetella pertussis* |
| Pyocin S killer protein | *Pseudomonas aeruginosa* |
| Ribosome inactivating protein family | *Escherichia coli* |
| *Salmonella* type III secretion SopE effector protein | *Salmonella* spp. |
| *Streptomyces* subtilisin inhibitor | *Streptomyces coelicolor* |
| Invasion protein B family | *Salmonella* spp. |
| *Salmonella* invasion protein InvJ | *Salmonella* spp. |
| Streptopain (C10) cysteine protease family | *Streptococcus pyogenes* |
| Subtilisin serine protease family (S8) | *Bacillus* spp. |
| Bacterial thiol-activated pore-forming cytolysin | *Streptococcus pyogenes* |
| Staphylococcal toxic shock syndrome toxin | *Staphylococcus aureus* |
| Translocated intimin receptor (Tir) | *Escherichia coli* |
| Type III secretion system outer membrane B protein family | *Shigella* spp. |
| Type IV secretion system CagA exotoxin | *Helicobacter pylori* |
| V8 serine protease family | *Staphylococcus aureus* |
| *Helicobacter pylori* vacuolating cytotoxin | *Helicobacter pylori* |
| *Yersinia* virulence determinant YopE protein | *Yersinia pestis* |
| *Yersinia* serine/threonine protein kinase | *Yersinia pestis* |
| TRANSPORTERS | |
| ABC-2 type transport system membrane protein | *Haemophilus influenzae* |
| *Salmonella/Yersinia* modular tyrosine phosphatase | *Salmonella* spp. |
| Bacterial general secretion pathway protein C | *Vibrio cholerae* |
| Bacterial general secretion pathway protein D | *Vibrio cholerae* |
| Bacterial general secretion pathway protein F | *Vibrio cholerae* |
| Bacterial general secretion pathway protein G | *Vibrio cholerae* |
| Bacterial general secretion pathway protein H | *Vibrio cholerae* |
| Gram-negative bacterial RTX toxin determinant A family | *Escherichia coli* |
| Gram-negative bacterial RTX toxin-activating protein C | *Escherichia coli* |
| Gram-negative bacterial RTX secretion protein D | *Escherichia coli* |
| SecA protein | *Escherichia coli* |
| Bacterial protein-transport SecB chaperone protein | *Escherichia coli* |
| Bacterial translocase SecE | *Escherichia coli* |
| Bacterial translocase SecF protein | *Escherichia coli* |
| Protein-export SecG membrane protein | *Escherichia coli* |
| Preprotein translocase SecY subunit | *Escherichia coli* |
| *Salmonella* surface presentation of antigen gene type M | *Salmonella* spp. |

TABLE 2-continued

| Signature Name | Example Species |
| --- | --- |
| Gram-negative bacterial type III secretion SycD chaperone | *Yersinia pestis* |
| Gram-negative bacterial type III secretion SycE chaperone | *Yersinia pestis* |
| Bacterial sec-independent translocation TatB protein | *Escherichia coli* |
| Gram-negative bacterial tonB protein | *Escherichia coli* |
| Type III secretion system inner membrane A protein family | *Salmonella* spp. |
| Type III secretion system inner membrane P protein family | *Salmonella* spp. |
| Type III secretion system inner membrane Q protein family | *Salmonella* spp. |
| Type III secretion system inner membrane R protein family | *Salmonella* spp. |
| Type III secretion system inner membrane S protein family | *Salmonella* spp. |
| Type III secretion system outer membrane G protein family | *Salmonella* spp. |
| Type III secretion system outer membrane K protein family | *Salmonella* spp. |
| Type III secretion system outer membrane O protein family | *Salmonella* spp. |
| Type IV secretion system CagX conjugation protein | *Helicobacter pylori* |
| SIDEROPHORES | |
| Ferric iron reductase | *Escherichia coli* |
| 2,3-dihydro-2,3-dihydroxybenzoate dehydrogenase | *Escherichia coli* |
| Enterobactin synthetase component D | *Escherichia coli* |
| Ferrichrome-binding periplasmic | *Escherichia coli* |
| Isochorismatase | *Escherichia coli* |
| MISCELLANEOUS | |
| Acetate kinase family | *Escherichia coli* |
| Acriflavin resistance protein family | *Escherichia coli* |
| Alanine racemase | *Escherichia coli* |
| Bacterial arginine deiminase | *Clostridium perfringens* |
| Bacterial arginine repressor | *Bacillus* spp. |
| Autoinducer synthesis protein | *Yersinia* spp. |
| Beta-lactamase class A | *Escherichia coli* |
| Bacterial carbamate kinase | *Pseudomonas aeruginosa* |
| DNA-binding protein FIS | *Escherichia coli* |
| Prokaryotic integration host factor | *Streptococcus* spp. |
| Hok/Gef cell toxic protein family | *Escherichia coli* |
| FIS bacterial regulatory protein HTH | *Escherichia coli* |
| TetR bacterial regulatory protein HTH | *Escherichia coli* |
| Lipopolysaccharide core biosynthesis protein | *Escherichia coli* |
| Bacterial autoinducer-2 (AI-2) production protein LuxS | *Escherichia coli* |
| Maltose binding protein | *Escherichia coli* |
| Bacterial mechano-sensitive ion channel | *Escherichia coli* |
| Metalloprotease inhibitor | *Pseudomonas* spp. |
| Hypothetical mycoplasma lipoprotein (MG045) | *Mycoplasma* app. |
| Gene IV protein | *Vibrio cholerae* |
| Phosphoenolpyruvate-protein phosphotransferase | *Legionella pneumophila* |
| *Salmonella* virulence plasmid 28.1 kDa A protein | *Salmonella* spp. |
| *Salmonella* virulence plasmid 65 kDa B protein | *Salmonella* spp. |
| Bacterial cell shape determinant MreB/Mbl protein | *Bacillus subtilis* |
| Tetracycline resistance protein | *Escherichia coli* |
| Tetracycline resistance protein TetB | *Streptococcus* spp. |
| Tetracycline resistance protein TetO/TetQ/TetM family | *Streptococcus* spp. |
| Tetracycline repressor protein | *Escherichia coli* |
| NON-BACTERIAL VIRULENCE FACTORS | |
| Alpha giardin | *Giardia lamblia* |
| Dense granule Gra2 protein | *Toxoplasma gondii* |
| Dense granule Gra6 protein | *Toxoplasma gondii* |
| Dense granule Gra7 protein | *Toxoplasma gondii* |
| MIC1 microneme protein | *Toxoplasma gondii* |

The invention claimed is:

1. A method of detecting a bacterial cell expressing a target gene comprising the steps of:
   a. introducing to said bacterial cell a nucleic acid construct encoding a portion of said target gene sequence, fused to an effector gene sequence, and a construct encoding an inhibitory nucleic acid sequence directed against at least said portion of said target gene sequence, wherein in the absence of said target gene, said inhibitory nucleic acid sequence supresses effector gene expression; and
   b. monitoring expression of said effector gene sequence in said cell and comparing the level of effector gene expression to a reference level, wherein if expression of said effector gene is increased relative to said reference level, said target gene is detected, thereby detecting the bacterial cell.

2. The method of claim 1, wherein the target gene is a mutant gene.

3. The method of claim 1, wherein said nucleic acid construct encoding a portion of said target gene sequence, fused to a said effector gene sequence, and said construct encoding an inhibitory nucleic acid sequence are encoded on the same nucleic acid molecule.

4. The method of claim 1, wherein the target gene is a drug resistance or virulence gene.

5. The method of claim 1, wherein the target gene is a viral gene.

6. The method of claim 1, wherein the effector gene sequence encodes a reporter molecule.

7. The method of claim 1, wherein the reporter comprises a polypeptide selected from the group consisting of an enzyme, a fluorescent polypeptide, a luminescent polypeptide and an antigen.

8. A method of detecting a eukaryotic cell expressing a target gene, the method comprising the steps of:
   a. introducing to said eukaryotic cell a nucleic acid construct encoding a portion of said target gene sequence fused to an effector gene sequence, and a construct encoding an inhibitory nucleic acid sequence directed against at least the portion of the target gene sequence, wherein in the absence of said target gene, the inhibitory nucleic acid sequence suppresses effector gene expression; and
   b. monitoring expression of the effector gene sequence in the cell and comparing the level of effector gene expression to a reference level, wherein if expression of the effector gene is increased relative to the reference level, the target gene is detected, thereby detecting the eukaryotic cell.

9. The method of claim 8, wherein the target gene is a mutant gene.

10. The method of claim 8, wherein the target gene is an oncogene or tumor associated gene.

11. The method of claim 8, wherein the target gene is a viral gene.

12. The method of claim 8, wherein the target gene is a multi-drug resistance transporter gene.

13. The method of claim 8, wherein the effector gene sequence encodes a reporter molecule.

14. The method of claim 8, wherein the reporter comprises a polypeptide selected from the group consisting of an enzyme, a fluorescent polypeptide, a luminescent polypeptide and an antigen.

15. The method of claim 1, wherein the inhibitory nucleic acid sequence comprises an antisense sequence.

16. The method of claim 8, wherein the inhibitory nucleic acid sequence comprises an RNA interference molecule.

* * * * *

SEQUENCE LISTING

```
<160> NUMBER OF SEQ ID NOS: 10

<210> SEQ ID NO 1
<211> LENGTH: 115
<212> TYPE: RNA
<213> ORGANISM: Artificial
<220> FEATURE:
<223> OTHER INFORMATION: Synthetic paired-termini construct.

<400> SEQUENCE: 1
aauugugagc ggauaacaau uucaggagga auuaaccaug caguggugu gguggguggub     60
```
ccauggcucg agcaccacca ccaccaccac ugcaugguua auuccuccua cuagu    115

<210> SEQ ID NO 2
<211> LENGTH: 660
<212> TYPE: DNA
<213> ORGANISM: Escherichia coli

<400> SEQUENCE: 2
atggagaaaa aaatcactgg atataccacc gttgatatat cccaatggca tcgtaaagaa    60
cattttgagg catttcagtc agttgctcaa tgtacctata accagaccgt tcagctggat   120
attacggcct ttttaaagac cgtaaagaaa aataagcaca gtttttatcc ggcctttatt   180
cacattcttg cccgcctgat gaatgctcat ccggaattcc gtatggcaat gaaagacggt   240
gagctggtga tatgggatag tgttcaccct tgttacaccg ttttccatga gcaaactgaa   300
acgttttcat cgctctggag tgaataccac gacgatttcc ggcagtttct acacatatat   360
tcgcaagatg tggcgtgtta cggtgaaaac ctggcctatt ccctaaaagg gtttattgag   420
aatatgtttt tcgtctcagc caatccctgg gtgagtttca ccagttttga tttaaacgtg   480
gccaatatgg acaacttctt cgcccccgtt ttcaccatgg gcaaatatta cgcaaggc    540
gacaaggtgc tgatgccgct ggcgattcag gttcatcatg ccgtctgtga tggcttccat   600
gtcggcagaa tgcttaatga attacaacag tactgcgatg agtggcaggg cggggcgtaa   660

<210> SEQ ID NO 3
<211> LENGTH: 624
<212> TYPE: DNA
<213> ORGANISM: Escherichia coli

<400> SEQUENCE: 3
atgtctagat tagataaaag taaagtgatt aacagcgcat tagagctgct taatgaggtc    60
ggaatcgaag gtttaacaac ccgtaaactc gcccagaagc taggtgtaga gcagcctaca   120
ttgtattggc atgtaaaaaa taagcgggct ttgctcgacg ccttagccat tgagatgtta   180
gataggcacc atactcactt tgccccttta aaggggaaaa gctggcaaga ttttttacgt   240
aataacgcta aagttttag atgtgcttta ctaagtcatc gcgatggagc aaaagtacat   300
ttaggtacac ggcctacaga aaaacagtat gaaactctcg aaaatcaatt agccttttta   360
tgccaacaag ttttttcact agagaatgca ttatatgcac tcagcgctgt ggggcatttt   420
actttaggtt gcgtattgga agatcaagag catcaagtcg ctaaagaaga aagggaaaca   480
cctactactg atagtatgcc gccattatta cgacaagcta tcgaattatt tgatcaccaa   540
ggtgcagagc cagccttctt attcggcctt gaattgatca tatgcggatt agaaaaacaa   600
cttaaatgtg aaagtgggtc ttaa                                          624

<210> SEQ ID NO 4
<211> LENGTH: 795
<212> TYPE: DNA
<213> ORGANISM: Streptomyces kanamyceticus

<400> SEQUENCE: 4
atgattgaac aagatggatt gcacgcaggt tctccggccg cttgggtgga gaggctattc    60
ggctatgact gggcacaaca gacaatcggc tgctctgatg ccgccgtgtt ccggctgtca   120
gcgcaggggc gcccggttct ttttgtcaag accgacctgt ccggtgccct gaatgaactg   180
caggacgagg cagcgcggct atcgtggctg gccacgacgg gcgttccttg cgcagctgtg   240
ctcgacgttg tcactgaagc gggaagggac tggctgctat tgggcgaagt gccggggcag   300

-continued

| | |
|---|---|
| gatctcctgt catctcacct tgctcctgcc gagaaagtat ccatcatggc tgatgcaatg | 360 |
| cggcggctgc atacgcttga tccggctacc tgcccattcg accaccaagc gaaacatcgc | 420 |
| atcgagcgag cacgtactcg gatggaagcc ggtcttgtcg atcaggatga tctggacgaa | 480 |
| gagcatcagg ggctcgcgcc agccgaactg ttcgccaggc tcaaggcgcg catgcccgac | 540 |
| ggcgaggatc tcgtcgtgac ccatggcgat gcctgcttgc cgaatatcat ggtggaaaat | 600 |
| ggccgctttt ctggattcat cgactgtggc cggctgggtg tggcggaccg ctatcaggac | 660 |
| atagcgttgg ctacccgtga tattgctgaa gagcttggcg gcgaatgggc tgaccgcttc | 720 |
| ctcgtgcttt acggtatcgc cgctcccgat tcgcagcgca tcgccttcta tcgccttctt | 780 |
| gacgagttct tctga | 795 |

<210> SEQ ID NO 5
<211> LENGTH: 861
<212> TYPE: DNA
<213> ORGANISM: Escherichia coli

<400> SEQUENCE: 5

| | |
|---|---|
| atgagtattc aacatttccg tgtcgccctt attcccttttt tgcggcatt ttgccttcct | 60 |
| gtttttgctc acccagaaac gctggtgaaa gtaaaagatg ctgaagatca gttgggtgca | 120 |
| cgagtgggtt acatcgaact ggatctcaac agcggtaaga tccttgagag ttttcgcccc | 180 |
| gaagaacgtt ttccaatgat gagcactttt aaagttctgc tatgtggcgc ggtattatcc | 240 |
| cgtattgacg ccgggcaaga gcaactcggt cgccgcatac actattctca gaatgacttg | 300 |
| gttgagtact caccagtcac agaaaagcat cttacggatg gcatgacagt aagagaatta | 360 |
| tgcagtgctg ccataaccat gagtgataac actgcggcca acttacttct gacaacgatc | 420 |
| ggaggaccga aggagctaac cgcttttttg cacaacatgg ggatcatgt aactcgcctt | 480 |
| gatcgttggg aaccggagct gaatgaagcc ataccaaacg acgagcgtga ccacacgatg | 540 |
| cctgtagcaa tggcaacaac gttgcgcaaa ctattaactg gcgaactact tactctagct | 600 |
| tcccggcaac aattaataga ctggatggag gcggataaag ttgcaggacc acttctgcgc | 660 |
| tcggcccttc cggctggctg gtttattgct gataaatctg gagccggtga gcgtgggtct | 720 |
| cgcggtatca ttgcagcact ggggccagat ggtaagccct cccgtatcgt agttatctac | 780 |
| acgacgggga gtcaggcaac tatggatgaa cgaaatagac agatcgctga gataggtgcc | 840 |
| tcactgatta agcattggta a | 861 |

<210> SEQ ID NO 6
<211> LENGTH: 1030
<212> TYPE: DNA
<213> ORGANISM: Enterococcus faecium

<400> SEQUENCE: 6

| | |
|---|---|
| atgaatagaa taaagttgc aatactgttt gggggttgct cagaggagca tgacgtatcg | 60 |
| gtaaaatctg caatagagat agccgctaac attaataaag aaaaatacga gccgttatac | 120 |
| attggaatta cgaaatctgg tgtatggaaa atgtgcgaaa aaccttgcgc ggaatgggaa | 180 |
| aacgacaatt gctattcagc tgtactctcg ccggataaaa aatgcacgg attacttgtt | 240 |
| aaaaagaacc atgaatatga aatcaaccat gttgatgtag cattttcagc tttgcatggc | 300 |
| aagtcaggtg aagatggatc catacaaggt ctgtttgaat tgtccggtat cccttttgta | 360 |
| ggctgcgata ttcaaagctc agcaatttgt atggacaaat cgttgacata catcgttgcg | 420 |

```
aaaaatgctg ggatagctac tcccgccttt tgggttatta ataaagatga taggccggtg      480
gcagctacgt ttacctatcc tgtttttgtt aagccggcgc gttcaggctc atccttcggt      540
gtgaaaaaag tcaatagcgc ggacgaattg gactacgcaa ttgaatcggc aagacaatat      600
gacagcaaaa tcttaattga gcaggctgtt tcggctgtg aggtcggttg tgcggtattg       660
ggaaacagtg ccgcgttagt tgttggcgag gtggaccaaa tcaggctgca gtacggaatc      720
tttcgtattc atcaggaagt cgagccgaaa aaaggctctg aaaacgcagt tataaccgtt      780
cccgcagacc tttcagcaga ggagcgagga cggatacagg aaacggcaaa aaaaatatat      840
aaagcgctcg gctgtagagg tctagcccgt gtggatatgt ttttacaaga taacggccgc      900
attgtactga acgaagtcaa tactctgccc ggtttcacgt catacagtcg ttatccccgt      960
atgatggccg ctgcaggtat tgcacttccc gaactgattg accgcttgat cgtattagcg     1020
ttaaagggt                                                             1030

<210> SEQ ID NO 7
<211> LENGTH: 969
<212> TYPE: DNA
<213> ORGANISM: Enterococcus faecium

<400> SEQUENCE: 7
atgaataaca tcggcattac tgtttatgga tgtgagcagg atgaggcaga tgcattccat       60
gctctttcgc ctcgctttgg cgttatggca acgataatta acgccaacgt gtcggaatcc      120
aacgccaaat ccgcgccttt caatcaatgt atcagtgtgg acataaaatc agagatttcc      180
gcctctattc ttcttgcgct gaagagagcc ggtgtgaaat atatttctac ccgaagcatc      240
ggctgcaatc atatagatac aactgctgct aagagaatgg gcatcactgt cgacaatgtg      300
gcgtactcgc cggatagcgt tgccgattat actatgatgc taattcttat ggcagtacgc      360
aacgtaaaat cgattgtgcg ctctgtggaa aaacatgatt tcaggttgga cagcgaccgt      420
ggcaaggtac tcagcgacat gacagttggt gtggtgggaa cgggccagat aggcaaagcg      480
gttattgagc ggctgcgagg atttggatgt aaagtgttgg cttatagtcg cagccgaagt      540
atagaggtaa actatgtacc gtttgatgag ttgctgcaaa atagcgatat cgttacgctt      600
catgtgccgc tcaatacgga tacgcactat attatcagcc acgaacaaat acagagaatg      660
aagcaaggag catttcttat caatactggg cgcggtccac ttgtagatac ctatgagttg      720
gttaaagcat tagaaaacgg gaaactgggc ggtgccgcat ggatgtatt ggaaggagag       780 gaagagtttt tctactctga ttgcacccaa aaaccaattg ataatcaatt tttacttaaa      840
cttcaaagaa tgcctaacgt gataatcaca ccgcatacgg cctattatac cgagcaagcg      900
ttgcgtgata ccgttgaaaa aaccattaaa aactgtttgg attttgaaag gagacaggag      960
catgaatag                                                             969

<210> SEQ ID NO 8
<211> LENGTH: 609
<212> TYPE: DNA
<213> ORGANISM: Enterococcus faecium

<400> SEQUENCE: 8
atggaaatag gatttacttt tttagatgaa atagtacacg gtgttcgttg ggacgctaaa       60
tatgccactt gggataattt caccggaaaa ccggttgacg gttatgaagt aaatcgcatt      120
gtagggacat acgagttggc tgaatcgctt ttgaaggcaa aagaactggc tgctaccccaa     180 gggtacggat tgcttctatg ggacggttac cgtcctaagc gtgctgtaaa ctgttttatg      240
```

```
caatgggctg cacagccgga aaataacctg acaaaggaaa gttattatcc caatattgac      300
cgaactgaga tgatttcaaa aggatacgtg gcttcaaaat caagccatag ccgcggcagt      360
gccattgatc ttacgcttta tcgattagac acgggtgagc ttgtaccaat ggggagccga      420
tttgatttta tggatgaacg ctctcatcat gcggcaaatg aatatcatg caatgaagcg       480 caaaatcgca gacgtttgcg ctccatcatg gaaaacagtg ggtttgaagc atatagcctc     540
gaatggtggc actatgtatt aagagacgaa ccataccccca atagctattt tgatttcccc    600
gttaaataa                                                              609

<210> SEQ ID NO 9
<211> LENGTH: 2007
<212> TYPE: DNA
<213> ORGANISM: Staphylococcus aureus

<400> SEQUENCE: 9
atgaaaaaga taaaaattgt tccacttatt ttaatagttg tagttgtcgg gtttggtata       60 tattttatg cttcaaaaga taagaaatt aataatacta ttgatgcaat tgaagataaa       120
aatttcaaac aagtttataa agatagcagt tatatttcta aaagcgataa tggtgaagta     180
gaaatgactg aacgtccgat aaaaatatat aatagtttag gcgttaaaga tataaacatt     240
caggatcgta aataaaaaa agtatctaaa aataaaaaac gagtagatgc tcaatataaa      300
attaaaacaa actacggtaa cattgatcgc aacgttcaat ttaattttgt taagaagat      360 ggtatgtgga gttagattg ggatcatagc gtcattattc caggaatgca gaaagaccaa      420
agcatacata ttgaaaattt aaaatcagaa cgtggtaaaa tttagaccg aaacaatgtg     480 gaattggcca atacaggaac agcatatgag ataggcatcg ttccaaagaa tgtatctaaa    540
aaagattata agcaatcgc taaagaacta gtatttctg aagactatat caacaacaa       600 atggatcaaa attgggtaca agatgatacc ttcgttccac ttaaaaccgt taaaaaaatg    660
gatgaatatt taagtgattt cgcaaaaaa tttcatctta caactaatga aacagaaagt    720
cgtaactatc ctctaggaaa agcgacttca catctattag gttatgttgg tcccattaac    780
tctgaagaat taaaacaaaa agaatataaa ggctataaag atgatgcagt tattggtaaa    840
aagggactcg aaaaacttta cgataaaaag ctccaacatg aagatggcta tcgtgtcaca    900
atcgttgacg ataatagcaa tacaatcgca catacattaa tagagaaaaa gaaaaaagat    960
ggcaaagata ttcaactaac tattgatgct aaagttcaaa agagtattta taacaacatg   1020
aaaaatgatt atggctcagg tactgctatc caccctcaaa caggtgaatt attagcactt   1080
gtaagcacac cttcatatga cgtctatcca tttatgtatg gcatgagtaa cgaagaatat   1140
aataaattaa ccgaagataa aaaagaacct ctgctcaaca gttccagat tacaacttca    1200 ccaggttcaa ctcaaaaaat attaacagca atgattgggt taaataacaa acattagac    1260 gataaaacaa gttataaaat cgatggtaaa ggttggcaaa aagataaatc ttggggtggt   1320
tacaacgtta caagatatga agtggtaaat ggtaatatcg acttaaaaca agcaatagaa   1380
tcatcagata cattttctt tgctagagta gcactcgaat taggcagtaa gaaatttgaa    1440
aaaggcatga aaaaactagg tgttggtgaa gatataccaa gtgattatcc atttataat     1500 gctcaaattt caaacaaaaa tttagataat gaaatattat tagctgattc aggttacgga   1560
caaggtgaaa tactgattaa cccagtacag atcctttcaa tctatagcgc attagaaaat   1620
aatggcaata ttaacgcacc tcacttatta aaagacacga aaaacaaagt ttggaagaaa   1680
```

| | |
|---|---:|
| aatattattt ccaaagaaaa tatcaatcta ttaactgatg gtatgcaaca agtcgtaaat | 1740 |
| aaaacacata aagaagatat ttatagatct tatgcaaact taattggcaa atccggtact | 1800 |
| gcagaactca aaatgaaaca aggagaaact ggcagacaaa ttgggtggtt tatatcatat | 1860 |
| gataaagata atccaaacat gatgatggct attaatgtta aagatgtaca agataaagga | 1920 |
| atggctagct acaatgccaa aatctcaggt aaagtgtatg atgagctata tgagaacggt | 1980 |
| aataaaaaat acgatataga tgaataa | 2007 |

<210> SEQ ID NO 10
<211> LENGTH: 4261
<212> TYPE: DNA
<213> ORGANISM: artificial
<220> FEATURE:
<223> OTHER INFORMATION: Example gene sensor plasmid sequence

<400> SEQUENCE: 10

| | |
|---|---:|
| ctcgagtccc tatcagtgat agagattgac atccctatca gtgatagaga tactgagcac | 60 |
| atcagcagga cgcactgacc gaattcagga ggaattaacc atgcagtggt ggtggtggtg | 120 |
| gtgaagcttt ataggtacat tgagcaactg actgaaatgc ctcaaaatgt tctttacgat | 180 |
| gccattggga tatatcaacg gtggtatatc cagtgatttt tttctccatt ttagcttcct | 240 |
| tagctcctga aaatctcgat aactcaaaaa atacgcccgg tagtgatcgc tagccaccac | 300 |
| caccaccacc actgcatggt taattcctcc tcccggggga tcccatggta cgcgtggcat | 360 |
| caaataaaac gaaaggctca gtcgaaagac tgggcctttc gttttatctg ttgtttgtcg | 420 |
| gtgaacgctc tcctgagtag gacaaatccg ccgccctaga cctaggcgtt cggctgcggc | 480 |
| gagcggtatc agctcactca aaggcggtaa tacggttatc cacagaatca ggggataacg | 540 |
| caggaaagaa catgtgagca aaaggccagc aaaaggccag gaaccgtaaa aaggccgcgt | 600 |
| tgctggcgtt tttccatagg ctccgccccc ctgacgagca tcacaaaaat cgacgctcaa | 660 |
| gtcagaggtg gcgaaacccg acaggactat aaagatacca ggcgtttccc cctggaagct | 720 |
| ccctcgtgcg ctctcctgtt ccgaccctgc cgcttaccgg atacctgtcc gcctttctcc | 780 |
| cttcgggaag cgtggcgctt tctcaatgct cacgctgtag gtatctcagt tcggtgtagg | 840 |
| tcgttcgctc caagctgggc tgtgtgcacg aaccccccgt tcagcccgac cgctgcgcct | 900 |
| tatccggtaa ctatcgtctt gagtccaacc cggtaagaca cgacttatcg ccactggcag | 960 |
| cagccactgg taacaggatt agcagagcga ggtatgtagg cggtgctaca gagttcttga | 1020 |
| agtggtggcc taactacggc tacactagaa ggacagtatt tggtatctgc gctctgctga | 1080 |
| agccagttac cttcggaaaa agagttggta gctcttgatc cggcaaacaa accaccgctg | 1140 |
| gtagcggtgg ttttttttgtt tgcaagcagc agattacgcg cagaaaaaaa ggatctcaag | 1200 |
| aagatccttt gatcttttct acggggtctg acgctcagtg gaacgaaaac tcacgttaag | 1260 |
| ggattttggt catgactagt gcttggattc tcaccaataa aaaacgcccg gcggcaaccg | 1320 |
| agcgttctga acaaatccag atggagttct gaggtcatta ctggatctat caacaggagt | 1380 |
| ccaagcgagc tctcgaaccc cagagtcccg ctcagaagaa ctcgtcaaga aggcgataga | 1440 |
| aggcgatgcg ctgcgaatcg ggagcggcga taccgtaaag cacgaggaag cggtcagccc | 1500 |
| attcgccgcc aagctcttca gcaatatcac gggtagccaa cgctatgtcc tgatagcggt | 1560 |
| ccgccacacc cagccggcca cagtcgatga atccagaaaa gcggccattt tccaccatga | 1620 |
| tattcggcaa gcaggcatcg ccatgggtca cgacgagatc ctcgccgtcg ggcatgcgcg | 1680 |
| ccttgagcct ggcgaacagt tcggctggcg cgagcccctg atgctcttcg tccagatcat | 1740 |

```
cctgatcgac aagaccggct tccatccgag tacgtgctcg ctcgatgcga tgtttcgctt    1800
ggtggtcgaa tgggcaggta gccggatcaa gcgtatgcag ccgccgcatt gcatcagcca    1860
tgatggatac tttctcggca ggagcaaggt gagatgacag gagatcctgc cccggcactt    1920
cgcccaatag cagccagtcc cttcccgctt cagtgacaac gtcgagcaca gctgcgcaag    1980
gaacgcccgt cgtggccagc acgatagcc gcgctgcctc gtcctgcagt tcattcaggg    2040
caccggacag gtcggtcttg acaaaaagaa ccgggcgccc ctgcgctgac agccggaaca    2100
cggcggcatc agagcagccg attgtctgtt gtgcccagtc atagccgaat agcctctcca    2160
cccaagcggc cggagaacct gcgtgcaatc catcttgttc aatcatgcga aacgatcctc    2220
atcctgtctc ttgatcagat cttgatcccc tgcgccatca gatccttggc ggcaagaaag    2280
ccatccagtt tactttgcag ggcttcccaa ccttaccaga gggcgcccca gctggcaatt    2340
ccgacgtctt tgggcccaag gcccagtctt tcgactgagc ctttcgtttt atttgatgcc    2400
tggcagttcc ctactctcgc atggggagac cccacactac catcggcgct acggcgtttc    2460
acttctgagt tcggcatggg gtcaggtggg accaccgcgc tactgccgcc aggcaaattc    2520
tgtttctaga ttatttgtat agttcatcca tgccatgtgt aatcccagca gctgttacaa    2580
actcaagaag gaccatgtgg tctctctttt cgttgggatc tttcgaaagg gcagattgtg    2640
tggacaggta atggttgtct ggtaaaagga cagggccatc gccaattgga gtattttgtt    2700
gataatggtc tgctagttga acgcttccat cttcaatgtt gtgtctaatt ttgaagttaa    2760
ctttgattcc attcttttgt ttgtctgcca tgatgtatac attgtgtgag ttatagttgt    2820
attccaattt gtgtccaaga atgtttccat cttctttaaa atcaatacct tttaactcga    2880
ttctattaac aagggtatca ccttcaaact tgacttcagc acgtgtcttg tagttcccgt    2940
catctttgaa aaatatagtt ctttcctgta cataaccttc gggcatggca ctcttgaaaa    3000
agtcatgctg tttcatatga tctgggtatc tcgcaaagca ttgaacacca taaccgaaag    3060
tagtgacaag tgttggccat ggaacaggta gttttccagt agtgcaaata aatttaaggg    3120
taagttttcc gtatgttgca tcaccttcac cctctccact gacagaaaat ttgtgcccat    3180
taacatcacc atctaattca acaagaattg ggacaactcc agtgaaaagt tcttctcctt    3240
tacgcgcggc cgccgccccg ccctgccact catcgcagta ctgttgtaat tcattaagca    3300
ttctgccgac atggaagcca tcacagacgg catgatgaac ctgaatcgcc agcggcatca    3360
gcaccttgtc gccttgcgta taatatttgc ccatggtgaa aacgggggcg aagaagttgt    3420
ccatattggc cacgtttaaa tcaaaactgg tgaaactcac ccagggattg gctgagacga    3480
aaaacatatt ctcaataaac cctttaggga ataggccag gttttcaccg taacacgcca    3540
catcttgcga atatatgtgt agaaactgcc ggaaatcgtc gtggtattca ctccagagcg    3600
atgaaaacgt ttcagtttgc tcatggaaaa cggtgtaaca agggtgaaca ctatcccata    3660
tcaccagctc accgtctttc attgccatac ggaattccgg atgagcattc atcaggcggg    3720
caagaatgtg aataaaggcc ggataaaact tgtgcttatt tttctttacg gtctttaaaa    3780
aggccgtaat atccagctga acggtctggt tataggtaca ttgagcaact gactgaaatg    3840
cctcaaaatg ttcttttacga tgccattggg atatatcaac ggtggtatat ccagtgattt    3900
ttttctccat tttagcttcc ttagctcctg aaaatctcga taactcaaaa aatacgcccg    3960
gtagtgatcg tcgactatgg agaaacagta gagagttgcg ataaaaagcg tcaggtagga    4020
tccgctaatc ttatggataa aaatgctatg gcatagcaaa gtgtgacgcc gtgcaaataa    4080
```

```
tcaatgtgga cttttctgcc gtgattatag acacttttgt tacgcgtttt tgtcatggct    4140
ttggtcccgc tttgttacag aatgctttta ataagcgggg ttaccggttt ggttagcgag    4200
aagagccagt aaaagacgca gtgacggcaa tgtctgatgc aatatggaca attggtttct    4260
t                                                                    4261
```